(12) United States Patent
Rothstein et al.

(10) Patent No.: US 11,737,869 B2
(45) Date of Patent: Aug. 29, 2023

(54) INTEGRATED VALVE ASSEMBLY AND METHOD OF DELIVERING AND DEPLOYING AN INTEGRATED VALVE ASSEMBLY

(71) Applicant: Medtronic, Inc., Minneapolis, MN (US)

(72) Inventors: Paul Rothstein, Elk River, MN (US); Jeffrey Sandstrom, Scandia, MN (US); Geoffrey Orth, Sebastopol, CA (US)

(73) Assignee: Medtronic, Inc., Minneapolis, MN (US)

( * ) Notice: Subject to any disclaimer, the term of this patent is extended or adjusted under 35 U.S.C. 154(b) by 318 days.

(21) Appl. No.: 17/017,382

(22) Filed: Sep. 10, 2020

(65) Prior Publication Data

US 2020/0405481 A1    Dec. 31, 2020

Related U.S. Application Data

(62) Division of application No. 16/023,475, filed on Jun. 29, 2018, now Pat. No. 10,799,343, which is a
(Continued)

(51) Int. Cl.
*A61F 2/24* (2006.01)
*A61F 2/82* (2013.01)

(52) U.S. Cl.
CPC ...... *A61F 2/2418* (2013.01); *A61F 2002/826* (2013.01); *A61F 2002/828* (2013.01); *A61F 2220/0008* (2013.01); *A61F 2250/006* (2013.01)

(58) Field of Classification Search
CPC .. A61F 2/24; A61F 2/2418; A61F 2/07; A61F 2/82; A61F 2/856; A61F 2/86;
(Continued)

(56) References Cited

U.S. PATENT DOCUMENTS

| 3,574,865 A | 4/1971 | Hamaker |
| 3,997,923 A | 12/1976 | Possis |

(Continued)

FOREIGN PATENT DOCUMENTS

| CN | 101352376 A | 2/2009 |
| CN | 104055600 A | 9/2014 |

(Continued)

OTHER PUBLICATIONS

International Search Report issued in PCT/US2016/017743, dated May 4, 2016.
(Continued)

*Primary Examiner* — Seema Mathew
(74) *Attorney, Agent, or Firm* — Medler Ferro Woodhouse & Mills PLLC

(57) ABSTRACT

An integrated valve prosthesis includes an anchor stent, a tether component, and a valve component. The anchor stent includes a self-expanding tubular frame member configured to be deployed in the annulus of an aortic valve or the aorta. The valve component includes a valve frame and a prosthetic valve coupled to the valve frame, and is configured to be deployed within the anchor stent. The tether component includes a first end coupled to the anchor stent and a second end coupled to the valve frame. In the delivery configuration, the tether component extends in a first direction from the anchor stent to the valve component, and in the deployed configuration, the tether component extends in a second direction from the anchor stent to the valve component. The second direction is generally opposite the first direction. The tether component may set the location of the valve component relative to the anchor stent.

14 Claims, 20 Drawing Sheets

Related U.S. Application Data division of application No. 15/013,341, filed on Feb. 2, 2016, now abandoned.

(60) Provisional application No. 62/115,464, filed on Feb. 12, 2015.

(58) Field of Classification Search
CPC ........ A61F 2/89; A61F 2/90; A61F 2002/061; A61F 2002/067; A61F 2220/0025
See application file for complete search history.

(56) References Cited

U.S. PATENT DOCUMENTS

| | | |
|---|---|---|
| RE31,040 E | 9/1982 | Possis |
| 4,506,394 A | 3/1985 | Bedard |
| 4,705,516 A | 11/1987 | Barone et al. |
| 4,790,843 A | 12/1988 | Carpentier et al. |
| 5,032,128 A | 7/1991 | Alonso |
| 5,332,402 A | 7/1994 | Teitelbaum |
| 5,370,685 A | 12/1994 | Stevens |
| 5,716,370 A | 2/1998 | Williamson, IV et al. |
| 5,984,959 A | 11/1999 | Robertson et al. |
| 6,074,418 A | 6/2000 | Buchanan et al. |
| 6,106,550 A | 8/2000 | Magovern et al. |
| 6,217,611 B1 | 4/2001 | Klostermeyer |
| 6,419,696 B1 | 7/2002 | Ortiz et al. |
| 6,425,916 B1 | 7/2002 | Garrison et al. |
| 6,468,305 B1 | 10/2002 | Otte |
| 6,569,196 B1 | 5/2003 | Vesely |
| 6,730,121 B2 | 5/2004 | Ortiz et al. |
| 6,764,508 B1 | 7/2004 | Roehe et al. |
| 6,786,925 B1 | 9/2004 | Schoon et al. |
| 6,790,229 B1 | 9/2004 | Berreklouw |
| 6,846,325 B2 | 1/2005 | Liddicoat |
| 6,893,459 B1 | 5/2005 | Macoviak |
| 6,908,481 B2 | 6/2005 | Criber |
| 6,939,365 B1 | 9/2005 | Fogarty et al. |
| 6,964,684 B2 | 11/2005 | Ortiz et al. |
| 7,097,659 B2 | 8/2006 | Woolfson et al. |
| 7,147,663 B1 | 12/2006 | Berg et al. |
| 7,172,625 B2 | 2/2007 | Shu et al. |
| 7,186,265 B2 | 3/2007 | Sharkawy et al. |
| 7,291,168 B2 | 11/2007 | Macoviak et al. |
| 7,300,463 B2 | 11/2007 | Liddicoat |
| 7,311,730 B2 | 12/2007 | Gabbay |
| 7,381,220 B2 | 6/2008 | Macoviak et al. |
| 7,503,930 B2 | 3/2009 | Sharkawy et al. |
| 7,611,535 B2 | 3/2009 | Woolfson et al. |
| 7,513,909 B2 | 4/2009 | Lane et al. |
| 7,527,646 B2 | 5/2009 | Rahdert et al. |
| 7,578,843 B2 | 8/2009 | Shu |
| 7,597,711 B2 | 8/2009 | Drews et al. |
| 7,648,528 B2 | 1/2010 | Styre |
| 7,691,144 B2 | 4/2010 | Chang et al. |
| 7,708,775 B2 | 5/2010 | Rowe et al. |
| 7,717,955 B2 | 5/2010 | Lane et al. |
| 7,722,667 B1 | 5/2010 | Buchanan |
| 7,758,640 B2 | 7/2010 | Vesely |
| 7,771,469 B2 | 8/2010 | Liddicoat |
| 7,780,726 B2 | 8/2010 | Seguin |
| 7,887,583 B2 | 2/2011 | Macoviak |
| 7,951,197 B2 | 5/2011 | Lane et al. |
| 7,959,674 B2 | 6/2011 | Shu et al. |
| 7,981,153 B2 | 7/2011 | Fogarty et al. |
| 8,025,695 B2 | 9/2011 | Fogarty et al. |
| 8,083,793 B2 | 12/2011 | Lane et al. |
| 8,105,377 B2 | 1/2012 | Liddicoat |
| 8,163,013 B2 | 4/2012 | Machold et al. |
| 8,187,207 B2 | 5/2012 | Machold et al. |
| 8,512,396 B2 | 8/2013 | Styrc |
| 9,585,748 B2* | 3/2017 | Wright .................. A61F 2/2433 |
| 10,034,784 B2* | 7/2018 | Tang .......................... A61F 2/07 |
| 10,765,541 B2* | 9/2020 | Shahriari ................ A61F 2/856 |
| 10,888,414 B2* | 1/2021 | Quadri ...................... A61F 2/07 |
| 2003/0100940 A1* | 5/2003 | Yodfat ....................... A61F 2/01 623/1.15 |
| 2005/0137686 A1 | 6/2005 | Salahieh et al. |
| 2007/0016288 A1 | 1/2007 | Gurskis |
| 2007/0078510 A1 | 4/2007 | Ryan |
| 2007/0282436 A1 | 12/2007 | Pinchuk |
| 2008/0071363 A1 | 3/2008 | Tuval et al. |
| 2009/0030510 A1* | 1/2009 | Ho ................... A61B 17/12136 623/2.11 |
| 2009/0125098 A1* | 5/2009 | Chuter ...................... A61F 2/07 623/1.26 |
| 2009/0171456 A1 | 7/2009 | Kveen |
| 2009/0248143 A1* | 10/2009 | Laham .................. A61F 2/2418 623/1.26 |
| 2009/0264993 A1* | 10/2009 | Greenan ................... A61F 2/07 623/1.36 |
| 2009/0270965 A1* | 10/2009 | Sinha ........................ A61F 2/07 623/1.14 |
| 2009/0270971 A1 | 10/2009 | Xiao |
| 2010/0179648 A1 | 7/2010 | Richter et al. |
| 2010/0179649 A1 | 7/2010 | Richter et al. |
| 2010/0185275 A1 | 7/2010 | Richter et al. |
| 2010/0312333 A1 | 12/2010 | Navia et al. |
| 2011/0208283 A1 | 8/2011 | Rust |
| 2012/0101571 A1 | 4/2012 | Thambar |
| 2013/0144373 A1* | 6/2013 | Shahriari .................. A61F 2/07 623/1.13 |
| 2013/0172978 A1 | 7/2013 | Vidlund et al. |
| 2013/0261738 A1 | 10/2013 | Clague et al. |
| 2014/0194983 A1 | 7/2014 | Kovalsky et al. |
| 2014/0277387 A1* | 9/2014 | Aharon ..................... A61F 2/07 623/1.23 |
| 2014/0288639 A1 | 9/2014 | Gainer |
| 2014/0296969 A1 | 10/2014 | Tegels |
| 2014/0324160 A1* | 10/2014 | Benichou .............. A61F 2/2412 623/2.11 |
| 2014/0350660 A1 | 11/2014 | Cocks et al. |
| 2014/0379076 A1 | 12/2014 | Vidlund |
| 2015/0005874 A1 | 1/2015 | Vidlund |
| 2015/0025625 A1* | 1/2015 | Rylski ................... A61F 2/2412 623/2.14 |
| 2016/0022409 A1* | 1/2016 | Aharon ............ A61B 17/12136 623/1.24 |
| 2016/0081829 A1 | 3/2016 | Rowe |
| 2018/0064525 A1* | 3/2018 | Frid ........................ A61F 2/06 |
| 2018/0098837 A1* | 4/2018 | Shahriari .................. A61F 2/07 |
| 2018/0153677 A1* | 6/2018 | Perkins ..................... A61F 2/07 |
| 2018/0289474 A1 | 10/2018 | Rajagopal |
| 2018/0318071 A1 | 11/2018 | Lozonschi |
| 2019/0380825 A1* | 12/2019 | Perkins .................. A61F 2/064 |
| 2020/0297475 A1* | 9/2020 | Quadri ...................... A61F 2/07 |
| 2020/0306066 A1* | 10/2020 | Perkins ..................... A61F 2/07 |

FOREIGN PATENT DOCUMENTS

| | | |
|---|---|---|
| WO | 2006036690 A1 | 4/2006 |
| WO | 2007081820 A1 | 7/2007 |
| WO | 2007130537 A1 | 11/2007 |
| WO | 2011143263 A2 | 11/2011 |
| WO | 2012030598 A2 | 3/2012 |
| WO | 2013092715 A2 | 6/2013 |
| WO | 2013116785 A1 | 8/2013 |
| WO | 2014110019 A1 | 7/2014 |

OTHER PUBLICATIONS

Chinese Office Action dated Nov. 16, 2018 is corresponding China Appln. No. 201680009959.9.

* cited by examiner

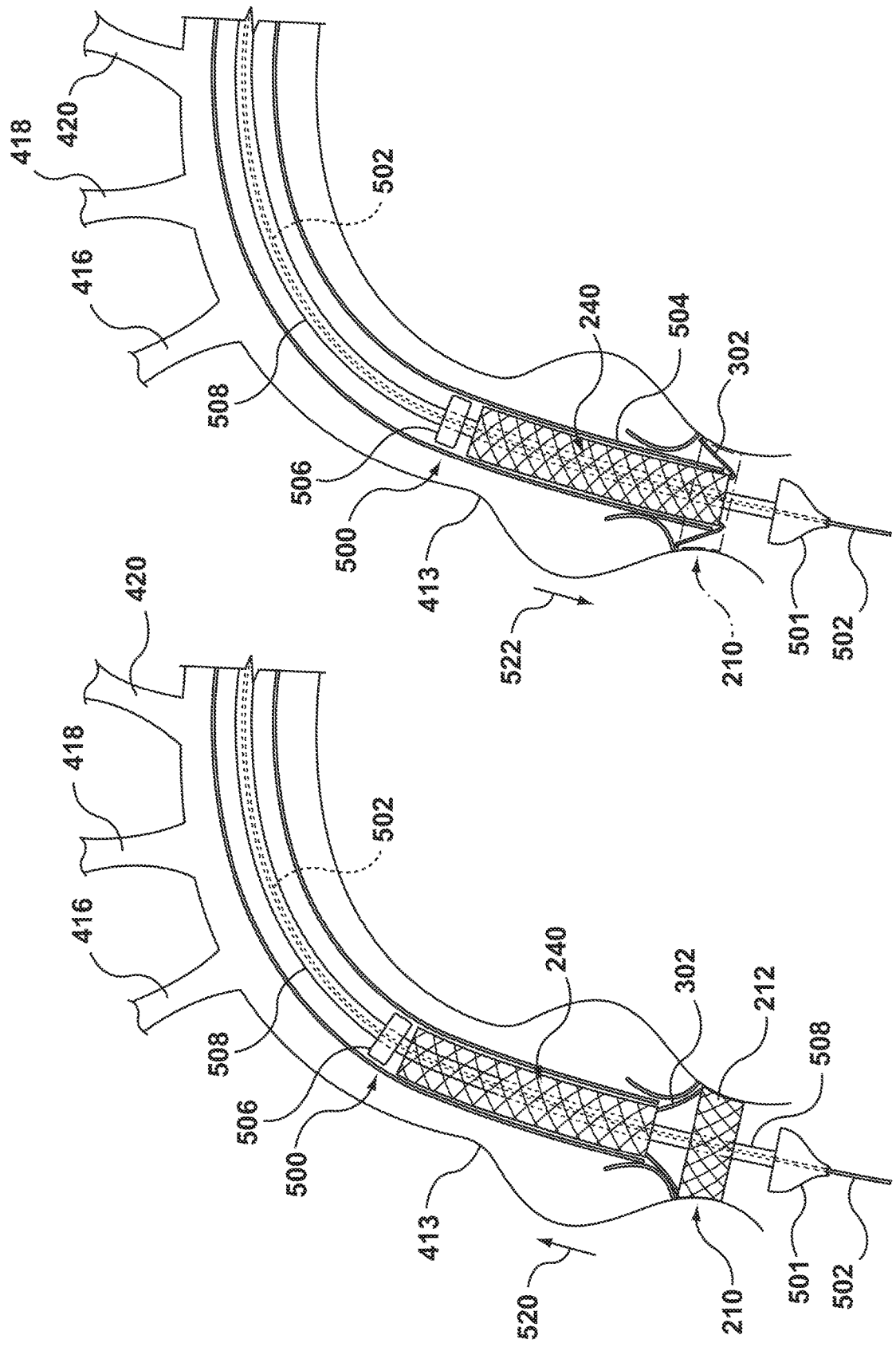

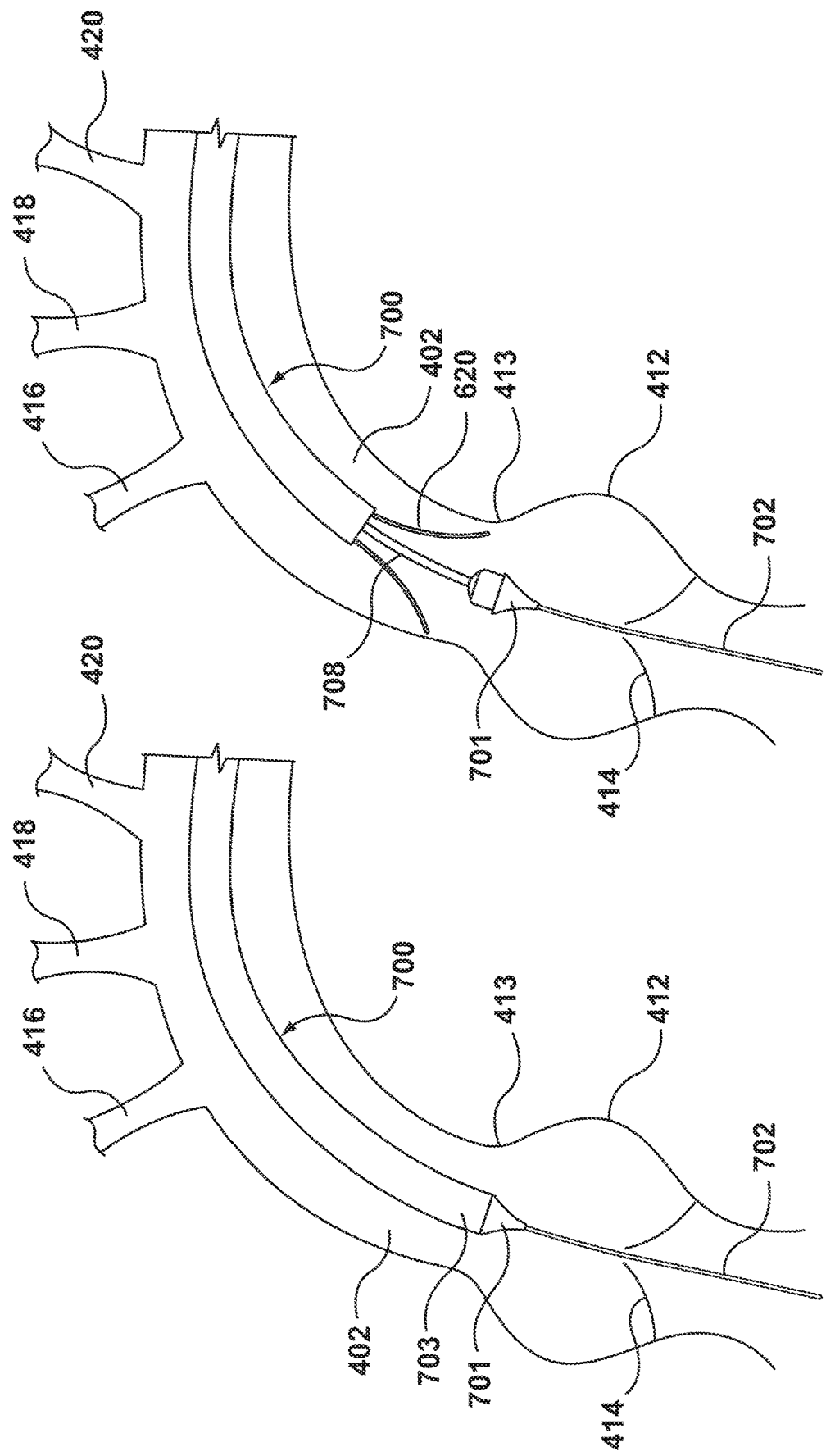

INTEGRATED VALVE ASSEMBLY AND METHOD OF DELIVERING AND DEPLOYING AN INTEGRATED VALVE ASSEMBLY

CROSS-REFERENCE TO RELATED APPLICATIONS

This application is a divisional application of U.S. patent application Ser. No. 16/023,475, filed Jun. 29, 2018, which is a divisional application of U.S. patent application Ser. No. 15/031,341, filed Feb. 2, 2016, now abandoned, which claims priority under 35 U.S.C. 119(e) to the benefit of the filing date of U.S. Provisional Application No. 62/115,464 filed Feb. 12, 2015, the contents of each of which are incorporated herein by reference in their entirety.

FIELD OF THE INVENTION

Embodiments hereof relate to heart valve prostheses and methods for intraluminally deploying heart valve prostheses, and in particular, to an integrated heart valve prosthesis including an anchor stent connected to a valve component and methods of intraluminally, delivering and deploying the integrated valve prosthesis.

BACKGROUND OF THE INVENTION

Heart valves, such as the mitral, tricuspid, aortic, and pulmonary valves, are sometimes damaged by disease or by aging, resulting in problems with the proper functioning of the valve. Heart valve problems generally take one of two forms: stenosis in which a valve does not open completely or the opening is too small, resulting in restricted blood flow; or insufficiency in which blood leaks backward across a valve when it should be closed.

Heart valve replacement has become a routine surgical procedure for patients suffering from valve regurgitation or stenotic calcification of the leaflets. Conventionally, the vast majority of valve replacements entail full sternotomy in placing the patient on cardiopulmonary bypass. Traditional open surgery inflicts significant patient trauma and discomfort, requires extensive recuperation times, and may result in life-threatening complications.

To address these concerns, efforts have been made to perform cardiac valve replacements using minimally-invasive techniques. In these methods, laparoscopic instruments are employed to make small openings through the patient's ribs to provide access to the heart. While considerable effort has been devoted to such techniques, widespread acceptance has been limited by the clinician's ability to access only certain regions of the heart using laparoscopic instruments.

Still other efforts have been focused upon percutaneous transcatheter (or transluminal) delivery of replacement cardiac valves to solve the problems presented by traditional open surgery and minimally-invasive surgical methods. In such methods, a valve prosthesis is compacted for delivery in a catheter and then advanced, for example through an opening in the femoral artery and through the descending aorta to the heart, where the prosthesis is then deployed in the valve annulus (e.g., the aortic valve annulus).

Various types and configurations of prosthetic heart valves are used in percutaneous valve procedures to replace diseased natural human heart valves. The actual shape and configuration of any particular prosthetic heart valve is dependent to some extent upon the valve being replaced (i.e., mitral valve, tricuspid valve, aortic valve, or pulmonary valve). In general, prosthetic heart valve designs attempt to replicate the function of the valve being replaced and thus will include valve leaflet-like structures used with either bioprostheses or mechanical heart valve prostheses. If bioprostheses are selected, the replacement valves may include a valved vein segment or pericardial manufactured tissue valve that is mounted in some manner within an expandable stent frame to make a valved stent. In order to prepare such a valve for percutaneous implantation, one type of valved stent can be initially provided in an expanded or uncrimped condition, then crimped or compressed around a balloon portion of a catheter until it is close to the diameter of the catheter. In other percutaneous implantation systems, the stent frame of the valved stent can be made of a self-expanding material. With these systems, the valved stent is crimped down to a desired size and held in that compressed state within a sheath, for example. Retracting the sheath from this valved stent allows the stent to expand to a larger diameter, such as when the valved stent is in a desired position within a patient.

While some problems of traditional open-heart surgery are overcome by percutaneous transcatheter (transluminal) methods, there are still risks associated with the method including patient prosthetic mismatch (PPM), para-valvular leakage, and conductance disorders. Many of these potential risks are thought to be aggravated by improper valve placement.

Patient prosthetic mismatch (PPM) is when an effective prosthetic valve area is less than that of a normal human valve. Despite technical efforts to optimize valve prostheses, their rheological properties are not comparable with those of native human valves and aortic stenosis will occur in a normally functioning prosthesis that is too small for the patient. Patient prosthetic mismatch is associated with decreased regression of left ventricular hypertrophy, reduced coronary flow reserve, increased incidence of congestive heart failure, diminished functional capacity, and increased risk of early and late mortality. Implantation of a prosthetic heart valve at an inaccurate depth is thought to increase the incidence and severity of patient prosthetic mismatch.

Para-valvular leakage (PVL) is leakage around an implanted prosthetic valve. The effects of para-valvular leakage on patients range from small PVL resulting in valve inefficiency and intravascular hemolysis causing anemia, to large PVL resulting in risk of heart failure and endocarditis. Often, sealing material is secured to the inside or outside of the stent frame to reduce the incidence of PVL, but the sealing material increases overall diameter (crossing profile) of the radially collapsed stent which limits crimping and may limit access through some vessels. Implantation of a prosthetic heart valve at an inaccurate depth is also thought to increase the incidence and severity of para-valvular leakage.

Conductance disorder is the abnormal progression of electrical impulses through the heart causing the heart to beat in an irregular fashion. The abnormal impulses may exhibit themselves as a mismatch of the electrical signals between sides or top to bottom and may cause symptoms from headaches, dizziness, and arrhythmia to cardiac arrest. Valve prostheses implanted too deep are thought to be more prone to inducing conduction disorders.

There is a need for devices and methods that allow for reduced crossing profile of a percutaneous transcatheter (transluminal) delivery of replacement heart valves while also providing sealing material to reduce para-valvular leakage (PVL). There is also a need for devices and methods to accurately locate and deploy valve prostheses to minimize para-valvular leakage (PVL), patient prosthesis mismatch (PPM), and conductance disorders in patients undergoing transcatheter valve implantation procedures.

BRIEF SUMMARY OF THE INVENTION

Embodiments hereof are related to an integrated valve assembly including an anchor stent, a tether component, and a valve component sequentially arranged within a delivery device. The anchor stent includes a self-expanding tubular frame member configured to be deployed in the annulus of an aortic valve. The valve component includes a valve frame configured to be deployed within the tubular frame member of the anchor stent such that the valve frame engages with the attachment members of the tubular frame member and a prosthetic valve coupled to the valve frame. The tether component is a plurality of tethers with a first end of the tether component coupled to the anchor frame and a second end of the tether component coupled to the valve frame. In the delivery configuration, the tether component extends in a first direction from the anchor stent to the valve component, and in the deployed configuration, the tether component extends in a second direction from the anchor stent to the valve component. The second direction is generally opposite the first direction.

Embodiments hereof are also directed to a method of implanting an integrated valve assembly at a location of a native heart valve. In an embodiment, the integrated valve assembly including an anchor stent, a valve component, and a tether component having a first end coupled to the anchor stent and a second end coupled to the valve component, is advanced in a delivery system in a radially compressed configuration into the annulus of a heart valve. The anchor stent includes a tubular frame member. The anchor stent is deployed in the annulus of the heart valve such that the tubular frame member expands from the radially compressed configuration to a radially expanded configuration engaging an inner wall surface of the annulus. Next, the tether component is exposed from the delivery system. The delivery system is advanced through the lumen of the anchor stent, effectively flipping the direction of the tether component. Accordingly, whereas the tether component in the delivery system initially extends in a first direction from the anchor stent towards the valve component, once flipped, the tether component extends in a second direction generally opposite from the first direction from the anchor stent towards the valve component. The delivery device is advanced until the tether component is taut. Tautness of the tether component correctly positions the valve component for deployment within the anchor stent. The valve component is then deployed. The valve component includes a valve frame and a prosthetic valve coupled to the valve frame. The valve component is deployed at the native aortic valve such that the valve frame expands from a radially compressed configuration to a radially expanded configuration with a proximal portion of the valve frame engaging an inner surface of the anchor stent.

In another embodiment, an integrated valve assembly includes an anchor stent, a valve component, a tether component, and a skirt. The tether component includes a first end coupled to the anchor stent, and a second end coupled to the skirt. The skirt has a first end coupled to the tether component and a second end coupled to the valve component. The integrated valve assembly is advanced in a radially compressed configuration into the aorta. The anchor stent includes a tubular frame member and a proximal arm component extending from a proximal end of the tubular frame member. The proximal arm component is deployed such that the proximal arm component expands from a radially compressed configuration to the radially expanded configuration engaging the inner wall surface of the aortic sinuses. The anchor stent is advanced until the proximal arm component bottoms at the nadir of the aortic valve leaflets. The anchor stent is deployed in the aorta near the sinotubular junction such that the tubular frame member expands from the radially compressed configuration to a radially expanded configuration engaging an inner wall surface of the ascending aorta. The tether component and skirt are released from the delivery system. The delivery system with the valve component disposed therein is advanced through the lumen of the anchor stent, effectively flipping the direction of the tethers and skirt. Accordingly, whereas the tether component and the skirt initially extend in a first direction from the anchor stent towards the valve component, once flipped, the tethers and skirt extend in a second, and generally opposite direction from the anchor stent towards the valve component. The delivery system is advanced until the tether component and the skirt are taut. Tautness of the tether component and the skirt correctly positions the valve component for deployment within the annulus of the native valve. The valve component includes a valve frame and a prosthetic valve coupled to the valve frame. The valve component is deployed at the native aortic valve such that the valve frame expands from a radially compressed configuration to a radially expanded configuration with a proximal portion of the valve frame engaging the native aortic annulus and a distal portion of the valve frame engaging an inner surface of the anchor stent.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIGS. 5-11, and 11A are schematic illustrations of an embodiment of a method for delivering and deploying the integrated prosthesis assembly of FIG. 3 at an aortic valve with the anchor stent deployed in the annulus.

FIGS. 16-23 are schematic illustrations of an embodiment of a method for delivering and deploying the integrated valve assembly of FIG. 14 at an aortic valve with the anchor stent deployed in the aorta.

DETAILED DESCRIPTION OF THE INVENTION

Specific embodiments of the present invention are now described with reference to the figures, wherein like reference numbers indicate identical or functionally similar elements. The terms "distal" and "proximal" when used in the following description to refer to a catheter or delivery system are with respect to a position or direction relative to the treating clinician. Thus, "distal" and "distally" refer to positions distant from or in a direction away from the clinician and "proximal" and "proximally" refer to positions near or in a direction toward the clinician. When the terms "distal" and "proximal" are used in the following description to refer to a device to be implanted into a vessel, such as an anchor stent or valve component, they are used with reference to the direction of blood flow from the heart. Thus, "distal" and "distally" refer to positions in a downstream direction with respect to the direction of blood flow and "proximal" and "proximally" refer to positions in an upstream direction with respect to the direction of blood flow.

Figure 1:
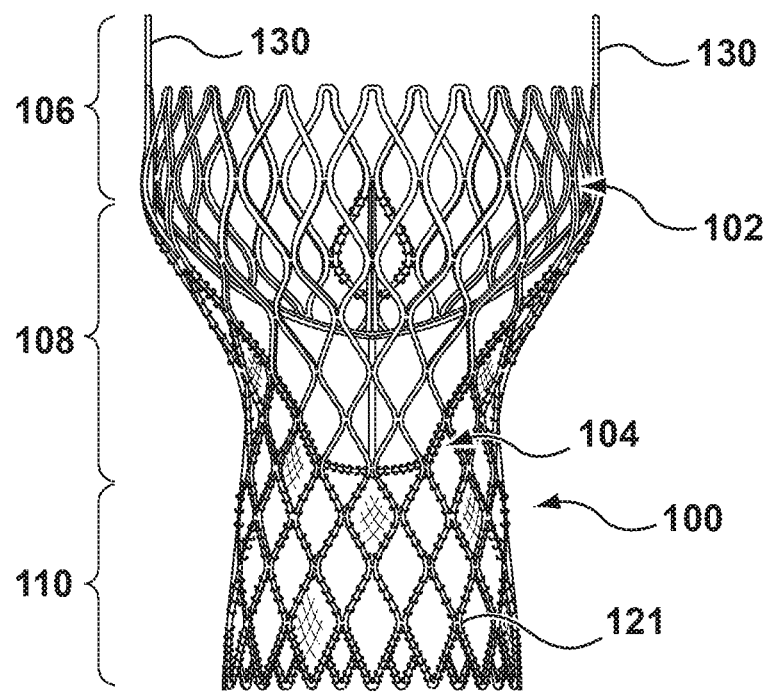
FIG. 1 is a schematic illustration of a prior art stented valve prosthesis.
Figure 2:
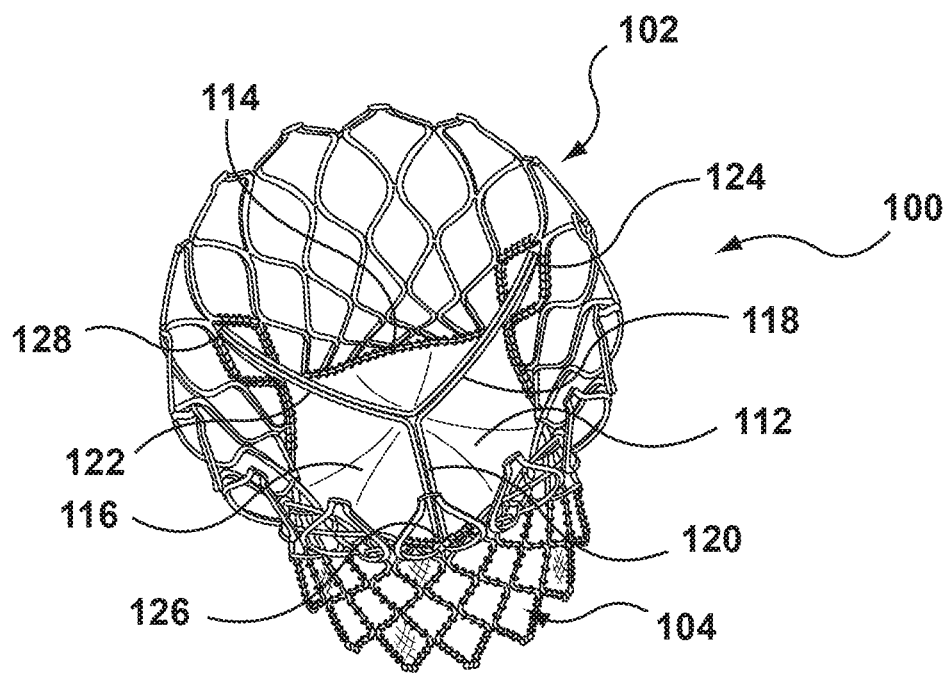
FIG. 2 is a schematic illustration of the prior art stented valve prosthesis of FIG. 1.

FIGS. 1 and 2 show an exemplary conventional valve prosthesis similar to the Medtronic CoreValve® transcatheter aortic valve replacement valve prosthesis and as described in U.S. Patent Application Publication No. 2011/0172765 to Nguyen et al. (hereinafter "the '765 publication"), which is incorporated by reference herein in its entirety. As shown in FIGS. 1 and 2, valve prosthesis 100 includes an expandable frame 102 having a valve body 104 affixed to its interior surface, e.g., by sutures. Frame 102 preferably comprises a self-expanding structure formed by laser cutting or etching a metal alloy tube comprising, for example, stainless steel or a shape memory material such as nickel titanium. The frame has an expanded deployed configuration which is impressed upon the metal alloy tube using techniques known in the art. Valve body 104 preferably comprises individual leaflets assembled to a skirt, where all of the components are formed from a natural or man-made material, including but not limited to, mammalian tissue, such as porcine, equine or bovine pericardium, or a synthetic or polymeric material.

Frame 102 in the exemplary embodiment includes an outflow section 106, an inflow section 110, and a constriction region 108 between the inflow and outflow sections. Frame 102 may comprise a plurality of cells having sizes that vary along the length of the prosthesis. When configured as a replacement for an aortic valve, inflow section 110 extends into and anchors within the aortic annulus of a patient's left ventricle and outflow section 106 is positioned in the patient's ascending aorta. Frame 102 also may include eyelets 130 for use in loading the heart valve prosthesis 100 into a delivery catheter.

Valve body 104 may include a skirt 121 affixed to frame 102, and leaflets 112, 114, 116. Leaflets 112, 114, 116 may be attached along their bases to skirt 121, for example, using sutures or a suitable biocompatible adhesive. Adjoining pairs of leaflets are attached to one another at their lateral ends to form commissures 124, 126, 128, with free edges 118, 120, 122 of the leaflets forming coaptation edges that meet in an area of coaptation, as described in the '765 application and shown in FIG. 2 hereof.

The following detailed description is merely exemplary in nature and is not intended to limit the invention or the application and uses of the invention. Although the description of the invention is in the context of transcatheter aortic valve implantation, the invention may also be used in any other body passageways where it is deemed useful. Furthermore, there is no intention to be bound by any expressed or implied theory presented in the preceding technical field, background, brief summary or the following detailed description.

Embodiments hereof are related to an integrated valve assembly including an anchor stent, a tether component, and a valve component assembled and connected together outside the human body. The tether component may be a plurality of tethers, a cylindrical skirt or a combination of thereof.

Figure 3:
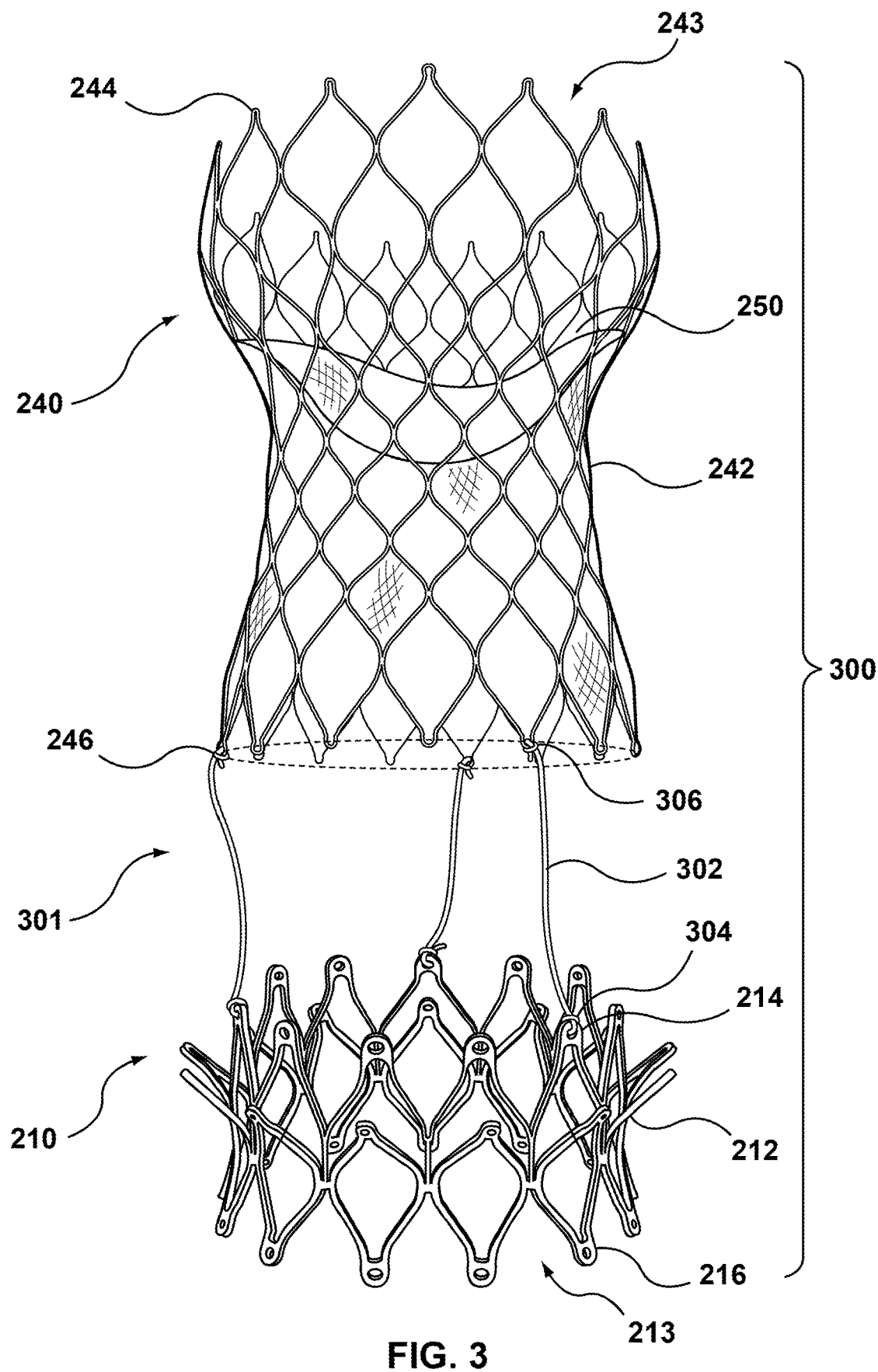
FIG. 3 is a schematic illustration of an integrated prosthesis assembly in accordance with an embodiment hereof.

In an embodiment shown in FIG. 3, an integrated valve assembly 300 includes an anchor stent 210, a tether component 301 and a valve component 240. Valve component 240 is sized and shaped to fit within a lumen of anchor stent 210, and anchor stent 210 is designed to deploy within the annulus of a heart valve, as described in more detail below.

Anchor stent 210 includes a frame 212 having a proximal end 216 and a distal end 214, as shown in FIG. 3. Frame 212 is a generally tubular configuration having a lumen 213. Frame 212 is a stent structure as is known in the art. Frame 212 may be self expanding or may be balloon expandable. Generally, frame 212 includes a first, radially compressed configuration for delivery and a second, radially expanded or deployed configuration when deployed at the desired site. In the radially expanded configuration, frame 212 may have a diameter in the range of 23 to 29 millimeters for use in the aortic annulus. However, it is recognized that frame 212 may have a smaller or larger expanded diameter depending on the application. Further, the unrestrained expanded diameter of self-expanding frames, such as frame 212, is generally about 2-5 millimeters larger than the diameter of the location in which the frame is to be installed, in order to create opposing radial forces between the outward radial force of the frame against an inward resisting force of the vessel.

Figure 3A:
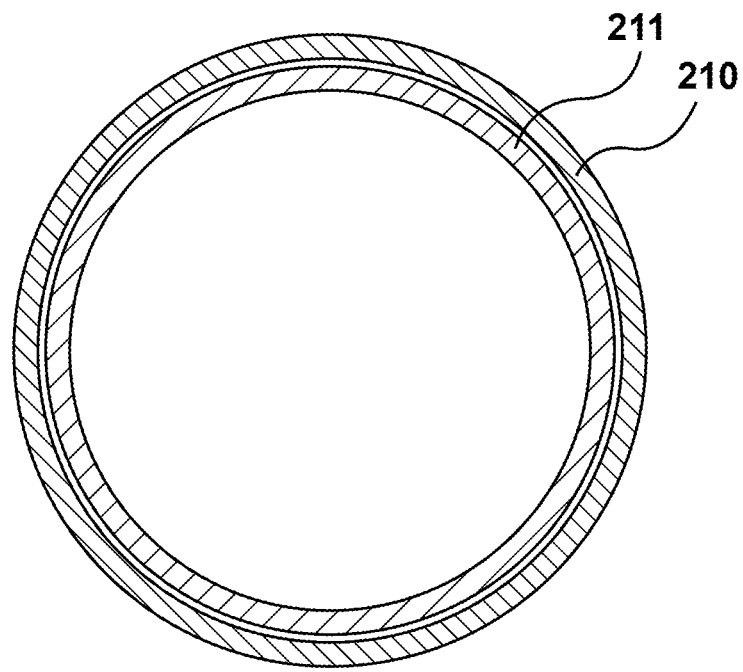
FIGS. 3A and 3B are a schematic cross-sectional illustrations of embodiments of an anchor stent with filler material on an inside surface or outside surface thereof.
Figure 3B:
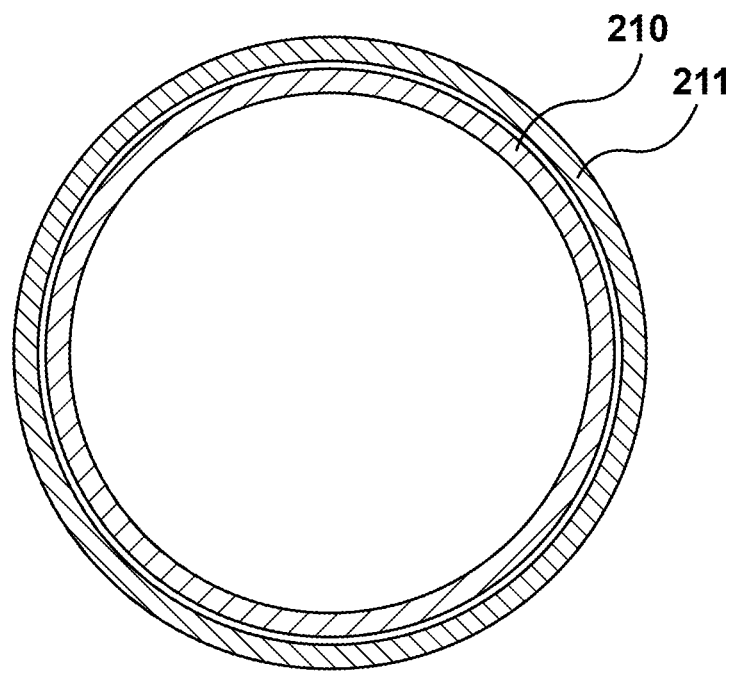

Anchor stent 210 may include a filler material 211 on an outside 213 surface of anchor stent 210, as shown in FIG. 3A, or the inside surface 215 of anchor stent 210, as shown in FIG. 3B, or both surfaces (not shown). Filler material 211 may be any anti-para-valvular leakage material suitable for the purposes described herein, such as, but not limited to, polyethylene terephthalate (PET), tissue (including porcine or bovine pericardium), or other biocompatible materials. The material may be woven or knitted. Filler material 211 may be secured to anchor stent 210 by methods such as, but not limited to, adhesives, sutures, laser or ultrasonic welding, or any other methods suitable for the purposes described herein.

Tether component 301 includes a plurality of tethers 302 as shown in FIG. 3. The embodiment of FIG. 3 shows three (3) tethers 302, however, it is understood that more or fewer tethers 302 may be provided depending on the specific requirements of the components, devices, and procedures being utilized. Tether component 301 has a first end 304 coupled to anchor stent 210, a second end 306 coupled to valve component 240, and a length that provides proper location placement of valve component 240 at the implantation site, as described in greater detail below. Tethers 302 are elongated members such as wires or sutures and may be constructed of materials such as, but not limited to, stainless steel, Nitinol, nylon, polybutester, polypropylene, silk, and polyester or other materials suitable for the purposes described herein. Tethers 302 may be connected to anchor frame 212 and valve frame 242 by methods such as, but not limited to fusing, welding, sutures or otherwise tied.

Valve component 240 includes a frame 242 and a prosthetic valve 250. Frame 242 is a generally tubular configuration having a proximal end 246, a distal end 244, and a lumen 243 there between. Frame 242 is a stent structure as is known in the art, and may be self-expanding or balloon expandable. Generally, frame 242 includes a first, radially compressed configuration for delivery and a second, radially expanded or deployed configuration when deployed at the desired site. In the radially expanded configuration, frame 242 may have a diameter in the range of 23 to 31 millimeters. However, it is recognized that frame 242 may have a smaller or larger expanded diameter depending on the application. Further, the unrestrained expanded diameter of self-expanding frames, such as frame 242, is generally about 2-5 millimeters larger than the diameter of the location in which the frame is to be installed, in order to create opposing radial forces between the outward radial force of the frame against an inward resisting force of the vessel. In the embodiment shown, distal end 244 has a larger expanded diameter than proximal end 246, similar to valve prosthesis 100 shown in FIGS. 1-2. However, frame 242 is not limited to such a configuration, and instead may have proximal and distal ends with similar expanded diameters. Further, frame 242 may have a smaller or larger expanded diameter depending on the application. Valve component 240 is configured to be disposed such that prosthetic valve 250 is disposed approximately at the location of the native aortic valve.

As explained briefly above and in more detail below, integrated valve assembly 300 includes anchor stent 210, tether component 301, and valve component 240. Anchor stent 210 is configured to be disposed in the annulus of the aortic valve. Valve component 240 is configured to be disposed such that prosthetic valve 250 is disposed approximately at the location of the native aortic valve with proximal end 246 of frame 242 separating the valve leaflets of the native aortic valve. Proximal end 246 of frame 242 extends into lumen 213 of frame 212 of anchor stent 210 and is held in place by the outward radial force of frame 242 and frictional forces between frame 242 of valve component 240 and frame 212 of anchor stent 210. Further, an inner surface of frame 212 and/or an outer surface of frame 242 may include locking features such as barbs, anti-migration tabs or other devices known to those skilled in the art to interconnect with anchor frame 212 and/or filler material 211

Figure 4:
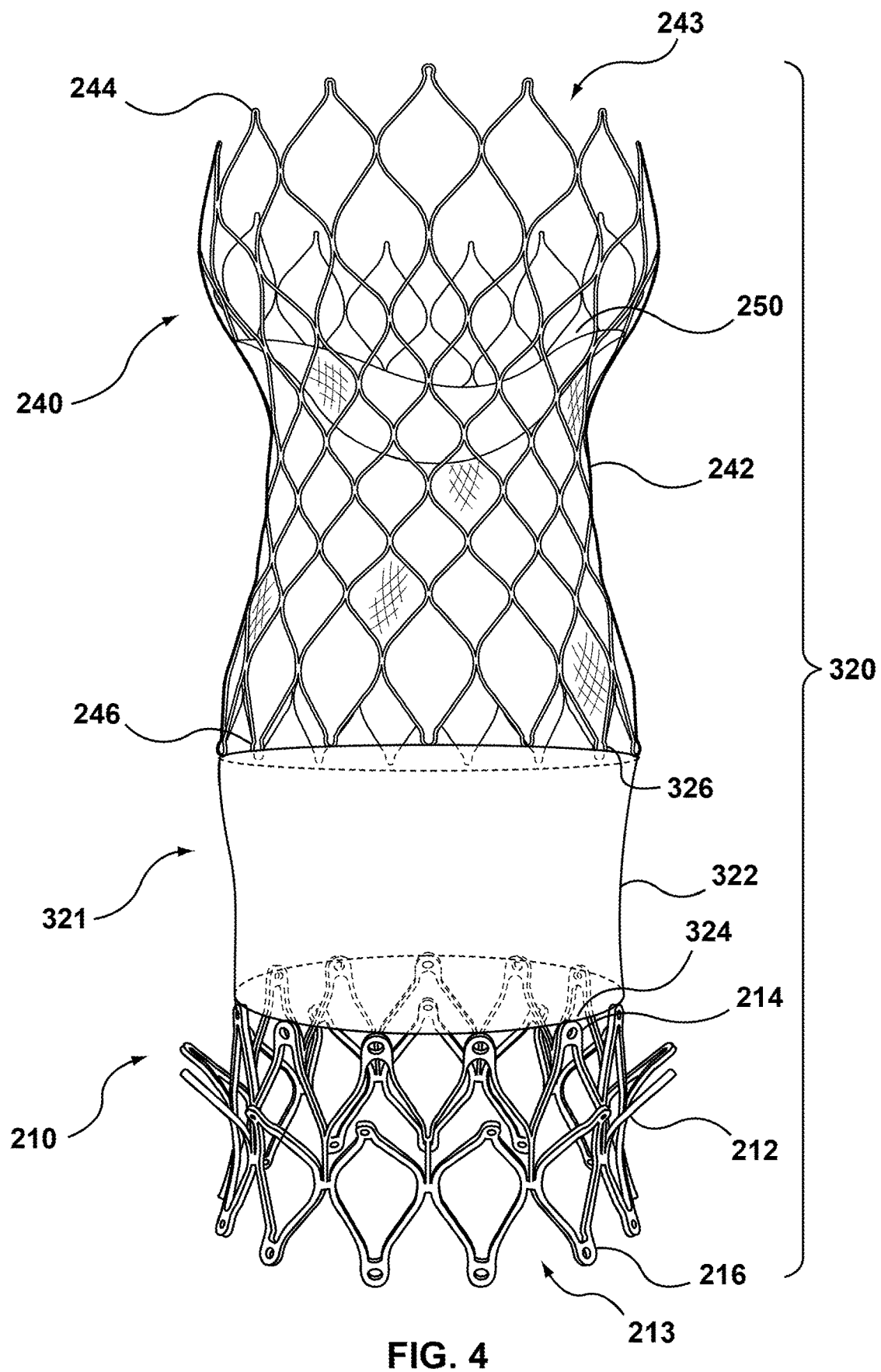
FIG. 4 is a schematic illustration of an integrated prosthesis assembly in accordance with another embodiment hereof.

FIG. 4 shows another embodiment of an integrated valve assembly 320 including anchor stent 210, a tether component 321 comprising a cylindrical skirt 322, and a valve component 240. Anchor stent 210 and valve component 240 may be as described above with respect to the embodiment of FIG. 3. Skirt 322 has a first end 324 coupled to anchor stent 210, a second end 326 coupled to valve component 240, and a length that provides proper placement of valve component 240 at the implantation site, as described in greater detail below. Skirt 322 is a cylindrical tube constructed of cloth or fabric material. The fabric may comprise any suitable material including, but not limited to, woven polyester such as polyethylene terephthalate, polytetrafluoroethylene (PTFE), tissue (such as porcine or bovine pericardium, or other biocompatible materials. Skirt 322 is secured to anchor frame 212 and valve frame 242 in a manner such as, but not limited to sutures, laser or ultrasonic welding, or other methods suitable for the purposes disclosed herein.

While embodiments of FIGS. 3 and 4 provide possible configurations for a tether component, they are not meant to limit the component to these configurations, and other materials, shapes, and combinations of skirts and/or tethers may be utilized. For example, and not by way of limitation, a skirt may be attached to an inside surface or outside surface of the tethers, or the tethers and the skirt may be connected sequentially. For example, and not by way of limitation, the tethers may be attached to the anchor stent and to the skirt with the skirt attached to the tethers and to the valve component.

FIGS. 5-11 and 11A schematically represent a method of delivering and deploying an integrated valve assembly in accordance with an embodiment hereof. FIGS. 5-11A describe the method with respect to integrated valve assembly 300 of FIG. 3. FIGS. 5-11A are not drawn to scale regarding relative lengths of anchor stent 210 and valve component 240.

Figure 5:
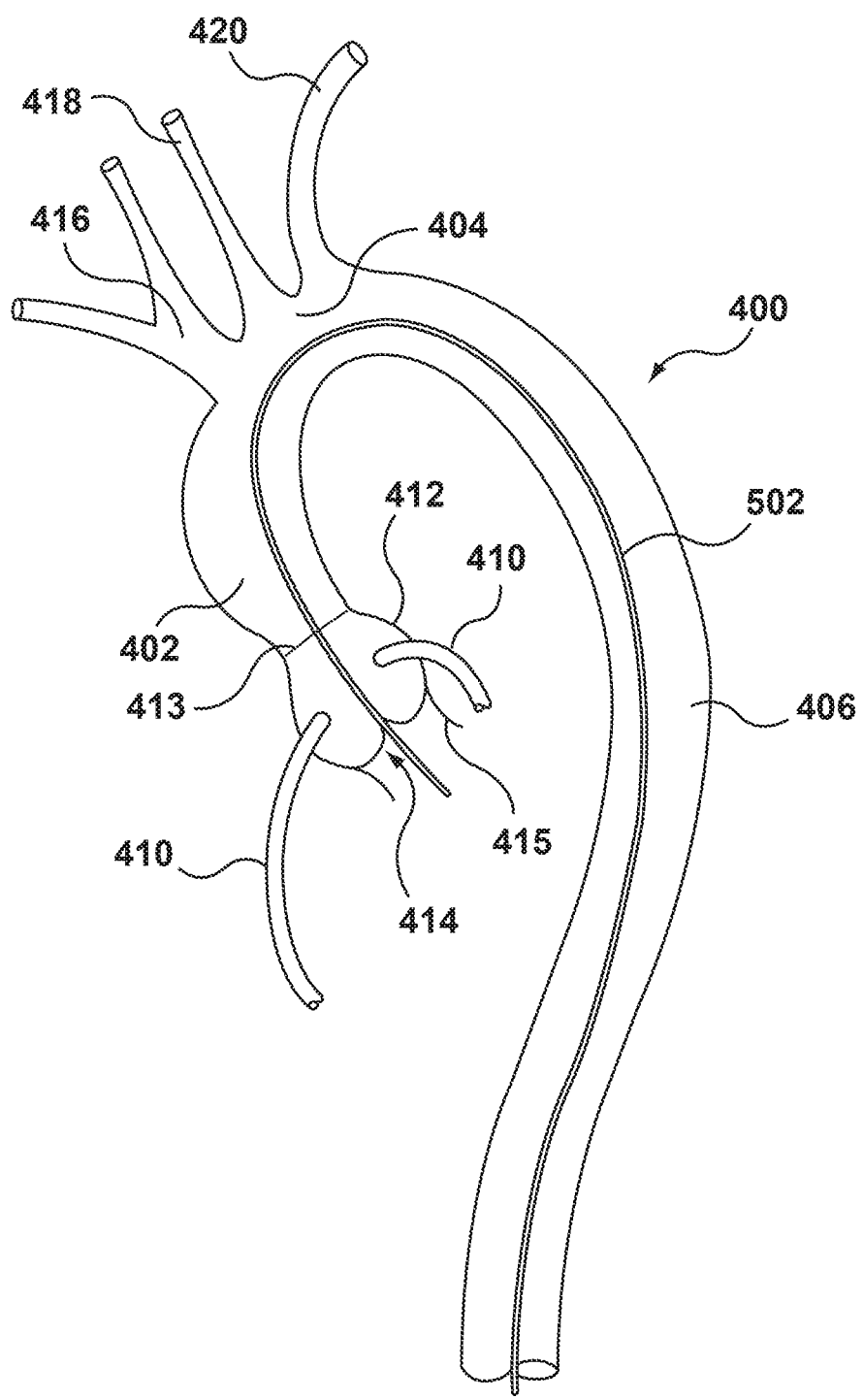

FIG. 5 shows a guidewire 502 advanced distally, i.e., away from the clinician, through the aorta 400 into the aortic sinuses 412 in the region of the aortic valve 414. Guidewire 502 may be introduced through an opening or arteriotomy through the wall of femoral artery in the groin region of the patient by methods known to those skilled in the art, such as, but not limited to, the Seldinger technique. Guidewire 502 is advanced into the descending (or abdominal) aorta 406, the aortic arch 404, and the ascending aorta 402, as shown in FIG. 5. FIG. 5 also shows three branch arteries emanating from aortic arch 404. In particular, the innominate or brachiocephalic artery 416, the left common carotid artery 418, and the left subclavian artery 420 emanate from aortic arch 404. The brachiocephalic artery 416 branches into the right common carotid artery and the right subclavian artery. Although FIGS. 5-11A show a retrograde percutaneous femoral procedure, it is not meant to limit the method of use and other procedural methods may be used. For example, and not by way of limitation, retrograde percutaneous implantation via subclavian/axillary routes, direct apical puncture, and the use of direct aortic access via either ministernotomy or right anterior thoracotomy may also be used.

Figure 6:
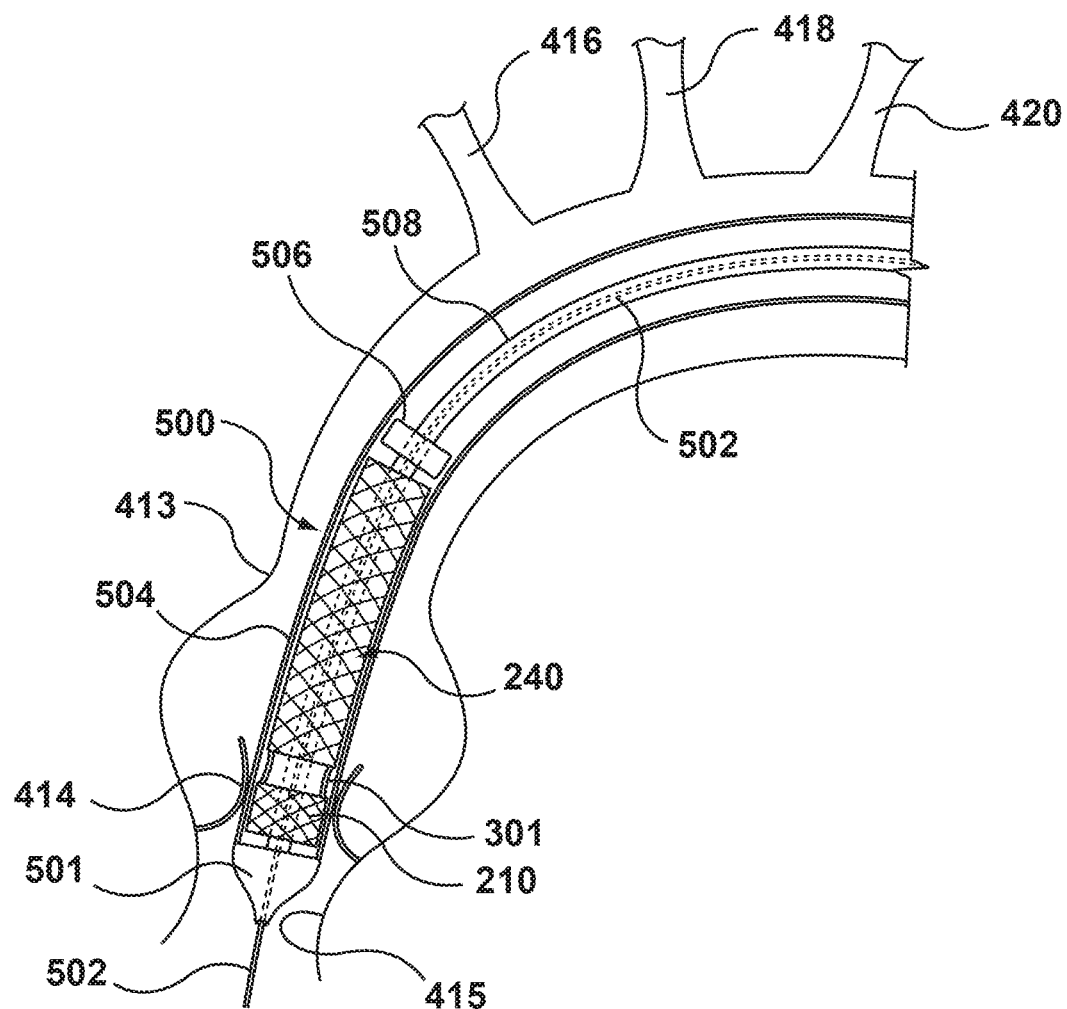

FIG. 6 shows a delivery system 500 for delivering integrated valve assembly 300 being advanced distally, i.e., away from the clinician, over guidewire 502 to a location in the annulus 415 of aortic valve 414. Delivery system 500 may be any suitable delivery system for delivering stents and/or stent grafts. In the embodiment shown schematically, anchor stent 210 is a self-expanding stent, tether component 301 is a plurality of tethers, and valve frame 242 of valve component 240 is a self-expanding stent. Accordingly, delivery system 500 generally includes an inner or guidewire shaft 508 which includes a guidewire lumen for receiving guidewire 502. A proximal end of guidewire 502 may be backloaded into the guidewire lumen of inner shaft 508 through a distal opening in inner shaft 508. Delivery system 500 may be an over-the-wire type catheter, or a rapid exchange catheter, or other catheter devices. Delivery system 500 further generally may include a distal tip 501, an outer sheath 504 that maintains anchor stent 210 and valve component 240 in the radially compressed or delivery configuration during intraluminal delivery through the vasculature, as shown in FIG. 6 and may also include a pusher or stopper 506, and other features. Delivery system 500 and/or anchor stent 210 may also include, for example, radiopaque markers such that the clinician may determine when delivery system 500 and/or anchor stent 210 is in the proper location for deployment.

Once delivery system 500 has been advanced to the desired location, such as when proximal end 216 of anchor stent is generally aligned with annulus 415, outer sheath 504 is retracted proximally, i.e., towards the clinician, as shown in FIG. 7. As outer sheath 504 is retracted, anchor frame 212 of anchor stent 210 expands radially outward, engaging the inner wall of annulus 415 of aortic valve 414, as shown in FIG. 7.

Outer sheath 504 is further retracted proximally, i.e., towards the clinician, to deploy tether component 301 from outer sheath 504. In other words, sheath 504 is retracted such that tether component 301 is no longer constrained by sheath 504. FIG. 7 shows tethers 302 deployed distal of anchor stent 210 and extending in a first direction 520 from anchor stent 210 toward valve frame 242.

Figure 9:
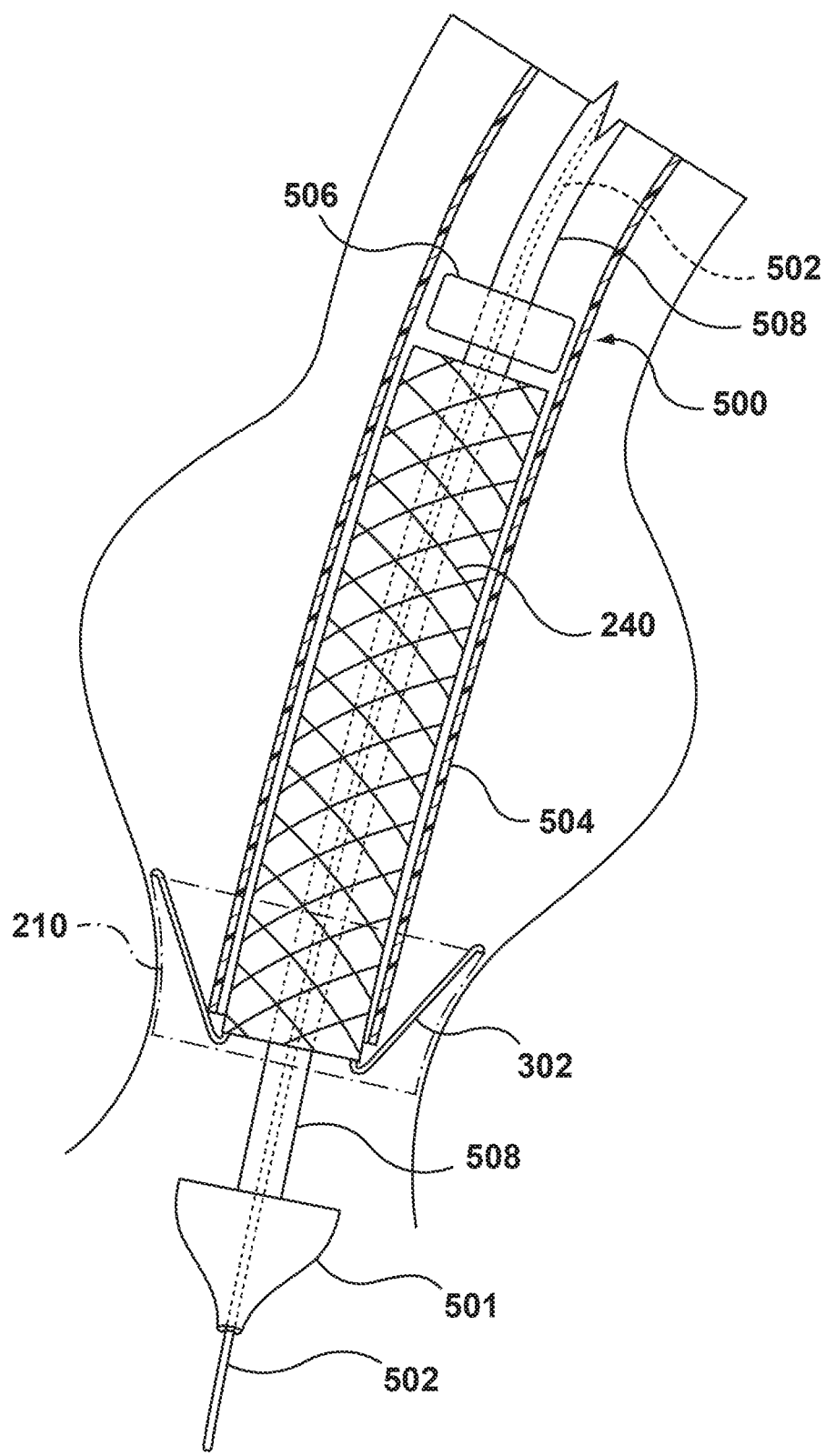

With outer sheath 504 retracted such that anchor stent 210 is deployed at the annulus 415 and tethers 302 are released from outer sheath 504, delivery system 500 is advanced distally, i.e., away from the clinician, through lumen 213 of anchor frame 212, pulling tethers 302 into lumen 213, effectively flipping the direction of tethers 302. Accordingly, whereas tethers 302 in FIG. 7 extend in a first direction 520 from anchor stent 210 towards valve component 240, tethers 302 in FIGS. 8-9 extend in a second direction 522 from anchor stent 210 towards valve component 240. Second direction 522 is generally opposite first direction 520. The term "generally opposite" with respect to directions described herein and terms similar thereto, as used herein, is not so narrow as to mean 180 degrees difference in direction. Instead, the term "generally opposite" with respect to direction means that a component includes a vector component in the first direction, the direction which is generally opposite includes a vector component in the opposite direction. Thus, the tethers 302 in the first direction 520 may be within 45 degrees of the first direction 520 and the second, generally opposite direction may be within 135 degrees to 225 degrees of the first direction 520. With delivery system 500 advanced into lumen 213 of anchor stent 210, tethers 302 reside within lumen 213 of anchor frame 212. Delivery system 500 is advanced until tethers 302 are taut. Tautness of tethers 302 correctly positions valve component 240 for deployment within anchor stent 210, as shown in FIGS. 8-9. Anchor stent 210 is shown with dotted lines for clarity of illustration in FIGS. 8-11A.

Figure 11:
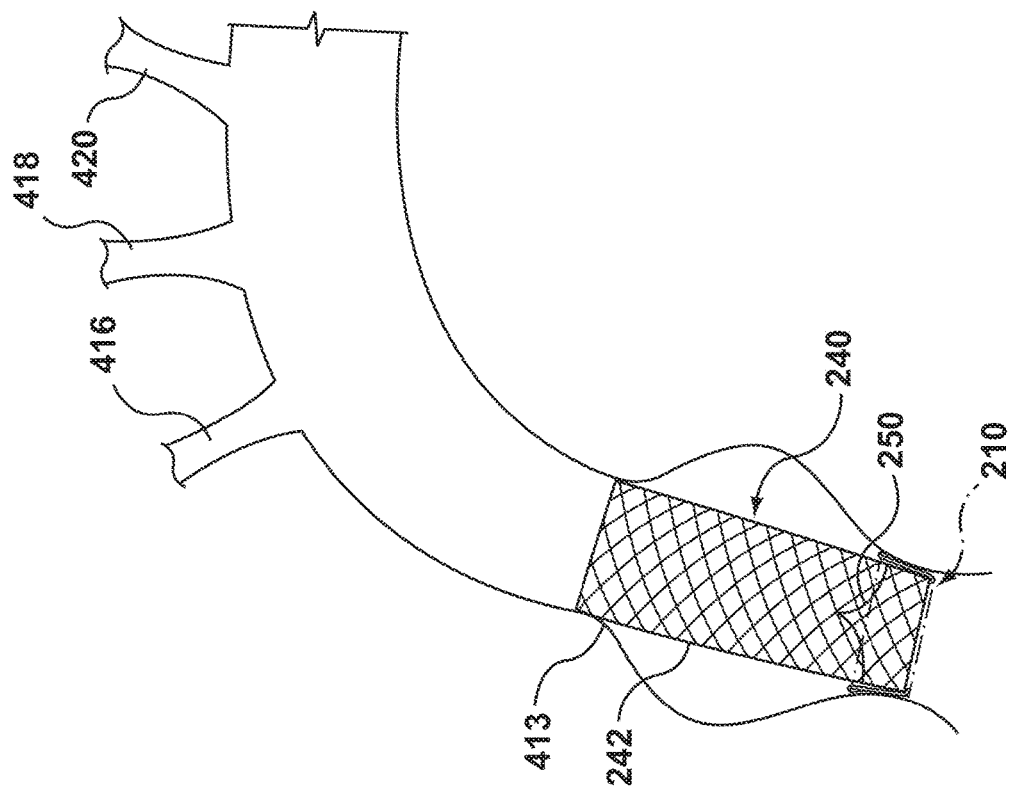
Figure 10:
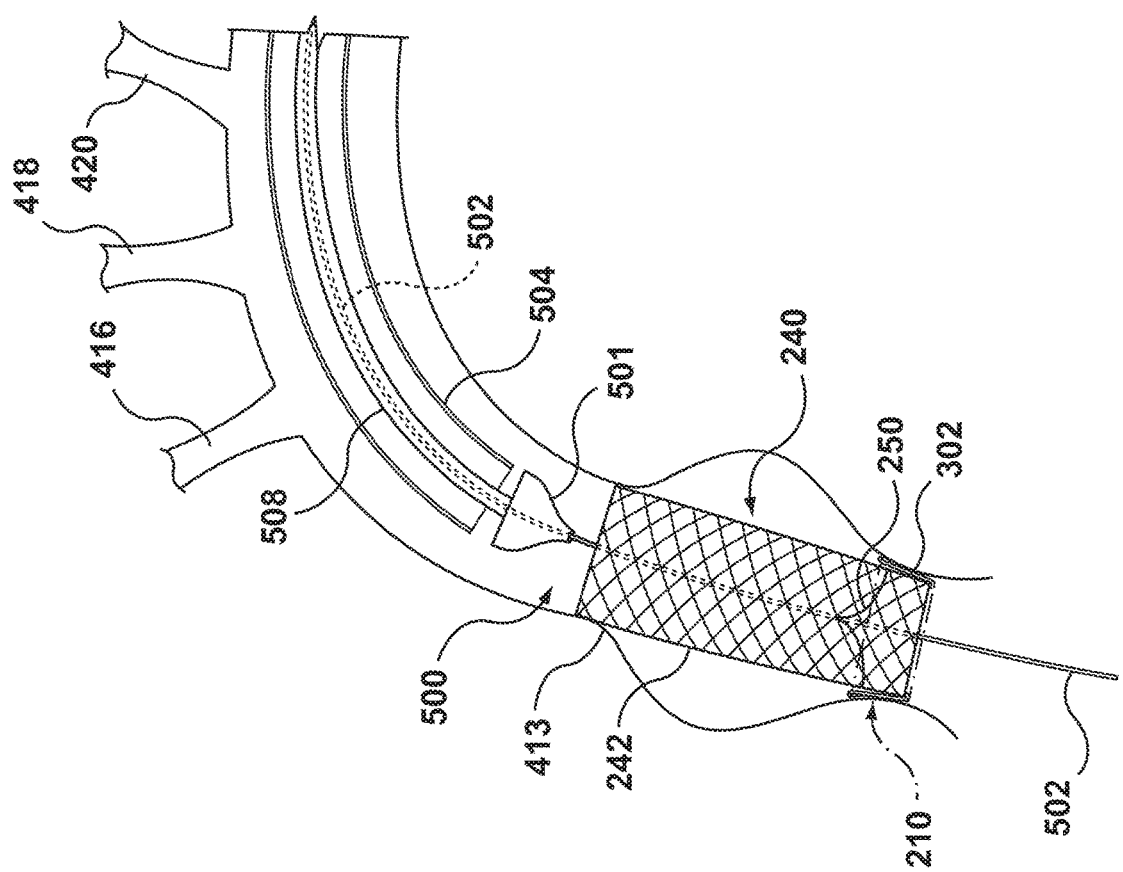
Figure 11A:
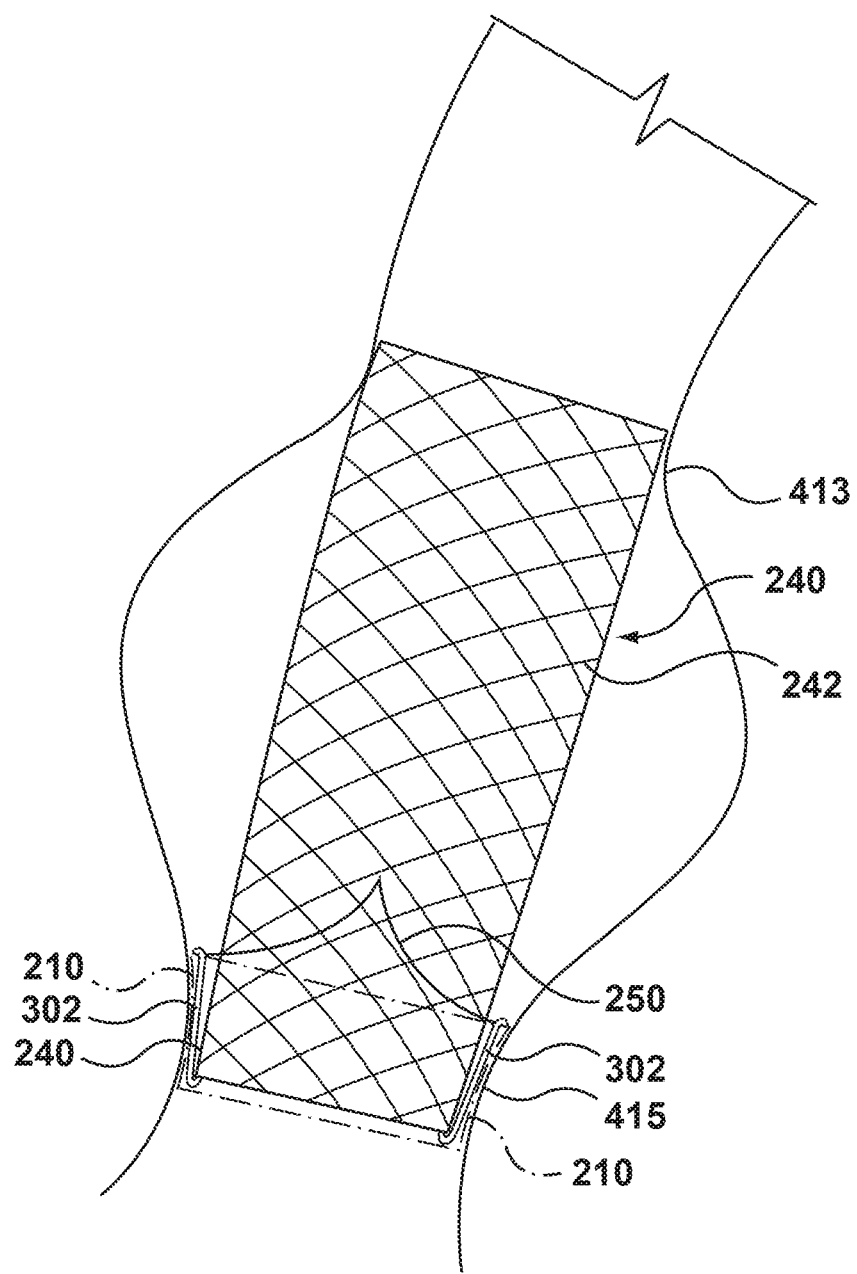

With tethers 302 taut and valve component 240 in proper alignment with anchor stent 210, sheath 504 is further retracted proximally, i.e., towards the clinician, and valve component 240 is deployed and expands radially outward, engaging the inner wall of the anchor frame 212 and sinotubular junction 413, as shown in FIGS. 10-11A. With integrated valve prosthesis assembly 300 fully deployed, delivery system 500 and guidewire 502 may be retracted proximally, i.e., towards the clinician, and removed in a manner consistent with current procedures know to those in the art. Integrated valve prosthesis 300 remains in the fully deployed configuration as shown in a close-up view of FIG. 11A.

Figure 12:
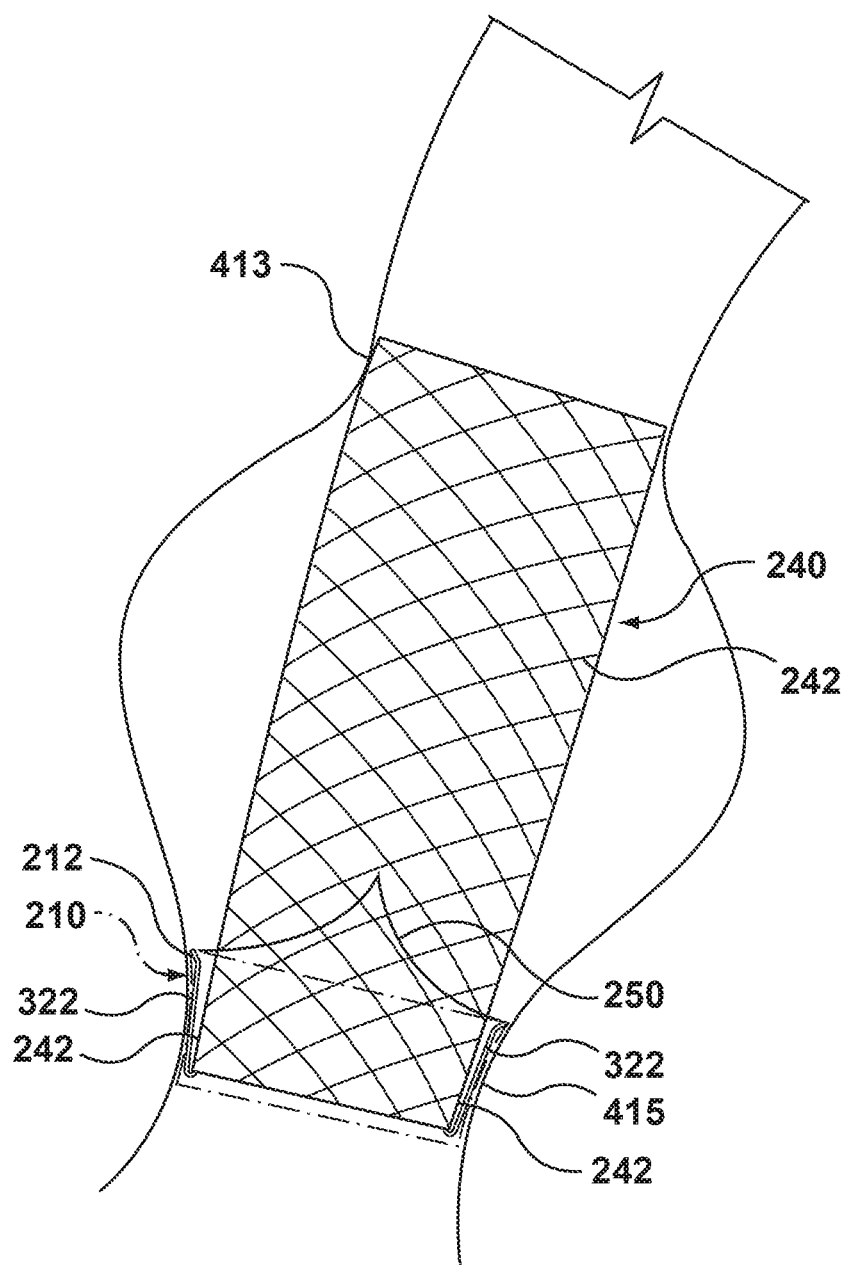
FIG. 12 is a schematic illustration of the integrated valve prosthesis assembly of FIG. 4 deployed at an aortic valve according to the method of FIGS. 5-11A.

While FIGS. 7-11A show the embodiment of FIG. 3 with tether component 301 as a plurality of tethers 302, the method above would be equally applicable to the embodiment of FIG. 4 with skirt 322. FIG. 12 shows integrated valve prosthesis 320 including skirt 322 deployed by the method as described with respect to FIGS. 5-11A.

Figure 13:
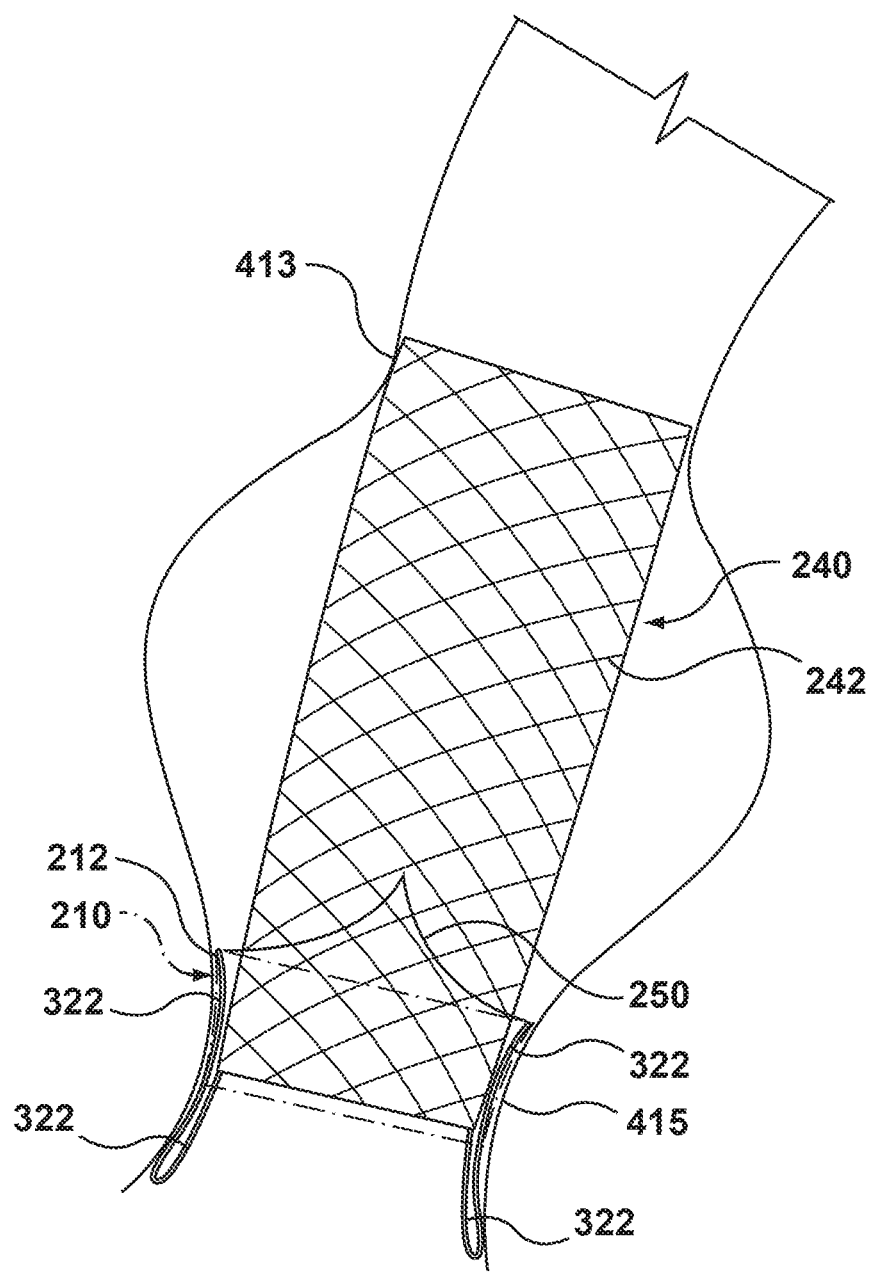
FIG. 13 is a schematic illustration of the integrated valve prosthesis assembly of FIG. 4 deployed at an aortic valve with the skirt component everted.

In another embodiment, integrated valve prosthesis 320 of FIG. 4 may be deployed such that skirt 322 everts and is folded proximal of anchor stent 210, as shown in FIG. 13. In such an embodiment, rather than the tautness of skirt 322 locating valve component 240, valve component 240 may be located by conventional methods such as, but not limited to, x-ray fluoroscopy, ultrasound imaging, electromagnetic tracking, or other methods suitable for the purposes disclosed herein. In order to deploy skirt 322 as shown in FIG. 13, the steps shown in FIGS. 5-7 are as described with respect to those figures. After skirt 322 is deployed as shown in FIG. 7 with respect to tethers 302, delivery system 500 is advanced distally. However, due to the length of skirt 322, delivery system 500 and skirt 322 extend through and beyond anchor stent 210. Delivery system 500 is then retracted such that proximal end 246 of valve component 240 is disposed within anchor stent 210 and skirt 322 folds as shown in FIG. 13. The remaining steps for deploying valve component 240 are as described with respect to FIGS. 10-11.

The close-up views described above show lateral gaps between the different parts which are disposed adjacent to each other. These gaps are shown for clarity such that the different parts of the integrated valve prosthesis and the heart valve may be seen. It is understood than many of these parts will abut directly against each other due to the radially outward forces of anchor stent 210 and valve frame 242.

Figure 14:
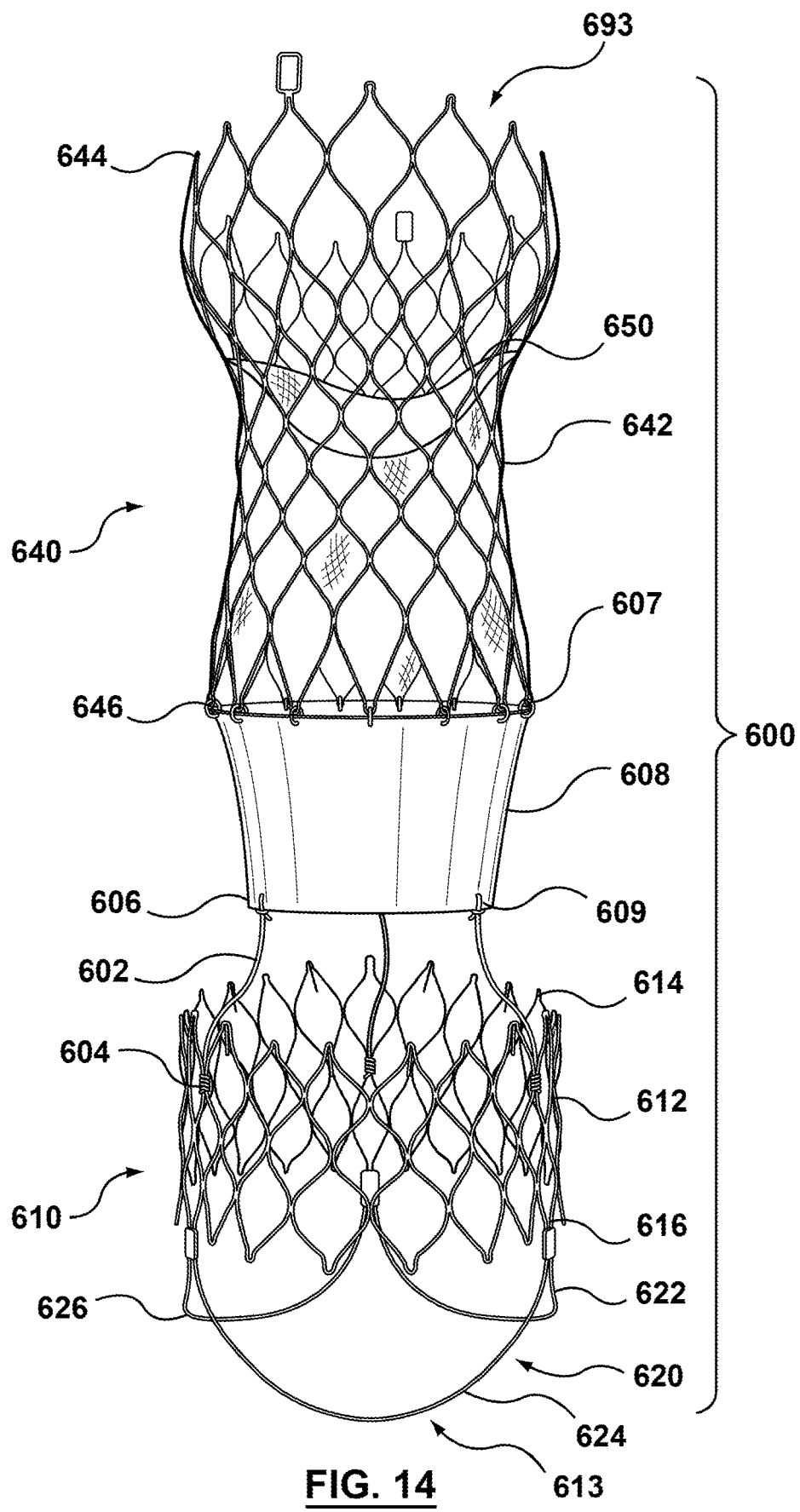
FIG. 14 is a schematic illustration of an integrated valve assembly in accordance with another embodiment hereof.

FIG. 14 shows schematically another embodiment of an integrated valve assembly 600 including an anchor stent 610, a plurality of tethers 602, a skirt 608, and a valve component 640. Valve component 640 is sized and shaped to fit within a lumen of anchor stent 610, and anchor stent 610 is designed to deploy in the aorta, as described in more detail below.

Anchor stent 610 includes a frame 612 having a proximal end 616 and a distal end 614, and a proximal arm component 620 extending proximally from proximal end 616 of frame 612, as shown in FIG. 14. Frame 612 is a generally tubular stent structure having a lumen 613, as described previously. Frame 612 may be self-expanding or may be balloon expandable. Generally, frame 612 includes a first, radially compressed configuration for delivery and a second, radially expanded or deployed configuration when deployed at the desired site. In the radially expanded configuration, frame 612 may have a diameter in the range of 23 to 31 millimeters. However, the expanded diameter may be a smaller or larger depending on the application. Further, as known those skilled in the art, the unrestrained expanded diameter of self-expanding frames, such as frame 612, is generally about 2-5 millimeters larger than the diameter of the vessel in which the frame is to be installed, in order to create opposing radial forces between the outward radial force of the frame against an inward resisting force of the vessel.

Figure 14A:
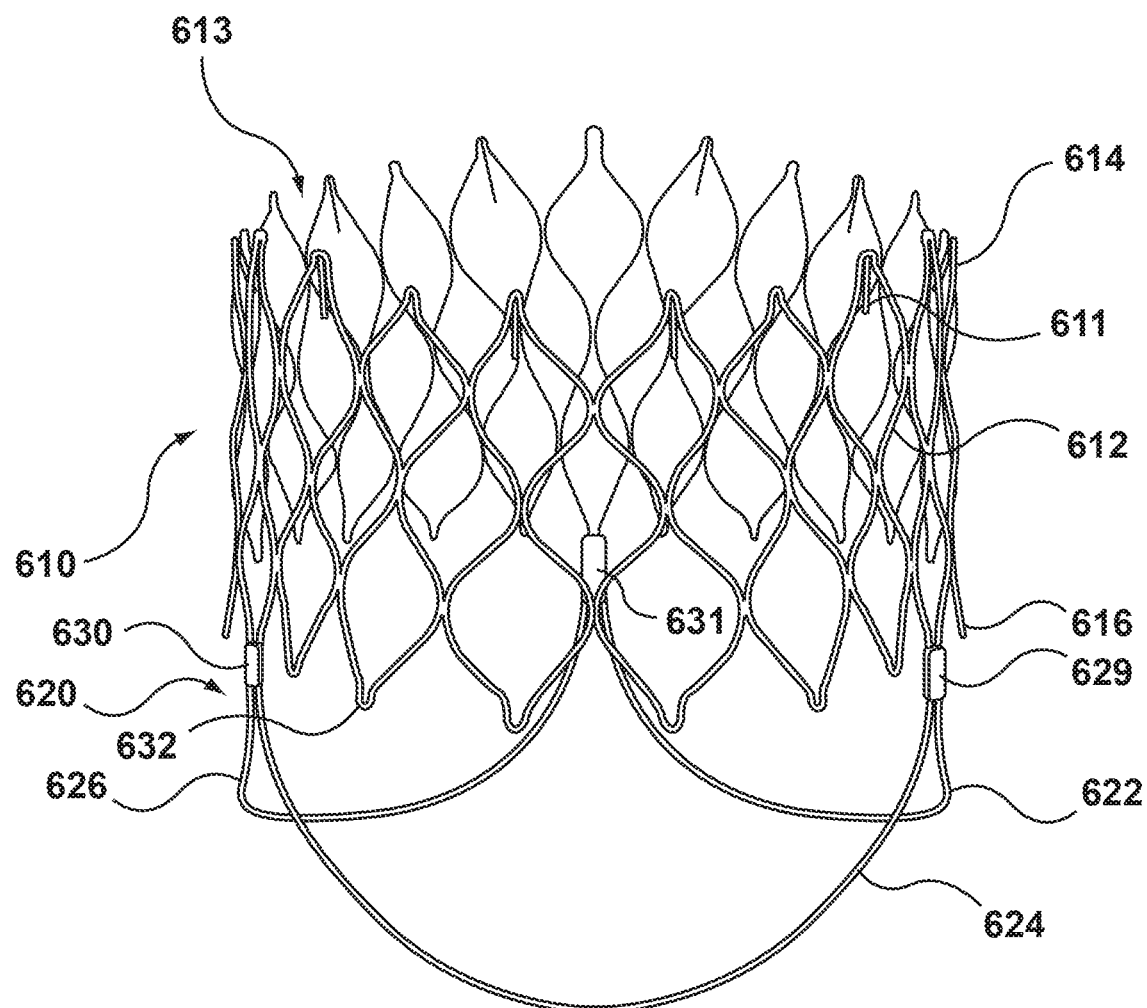
FIG. 14A is a schematic illustration of an anchor stent of the integrated valve assembly of FIG. 14.

Proximal arm component 620 extends proximally from proximal end 616 of frame 612. In the embodiment shown in FIG. 14, proximal arm component 620 includes a first arm 622, a second arm 624, and a third arm 626. In the embodiment shown in FIG. 14, each arm 622, 624, 626 is in the form of a wire loop with first and second ends of the wire attached to frame 612. In particular, first arm 622 includes first and second ends attached to frame 612 at connections 632, 633 respectively, as shown in FIG. 14A. Similarly, second arm 624 includes first and second ends attached to frame 612 at connections 628, 629, respectively, and third arm 626 includes first and second ends attached to frame 612 at connections 630, 631, respectively. Connections 628, 629, 630, 631, 632, 633 may be formed by the material of the arms and frame 612 fused or welded together. Alternatively, the connections may be mechanical connections such as, but not limited to, sutured or otherwise tied, a crimp connector to crimp ends of the arms to frame 612, or other suitable connections. Proximal arm component 620 includes a radially compressed configuration for delivery to the treatment site and a radially expanded or deployed configuration. In the radially expanded configuration, proximal arm component has a diameter in the range of 29 to 39 mm. However, the diameter may be smaller or larger depending on the application. As shown in FIG. 14, in the radially expanded configuration, arms 622, 624, and 626 flare outwardly from proximal end 616 of frame 612. Although proximal arm component 620 has been shown as having three arms with connections approximately equally spaced around the circumference of frame 612, more or fewer arms may be utilized, and the arms need not be equally spaced around the circumference of frame 612.

The embodiment of FIG. 14 shows three (3) tethers 602, however, it is understood that more or fewer tethers 602 may be provided depending on the specific requirements of the components, devices and procedures being utilized. Tethers 602 have a first end 604 coupled to anchor stent 610, a second end 606 coupled to skirt 608, and a length that provides proper location placement of valve component 640 at the implantation site, as described in greater detail below. Tethers 602 are elongated members such as wires or sutures and may be constructed of materials such as, but not limited to, stainless steel, Nitinol, nylon, polybutester, polypropylene, silk, and polyester or other materials suitable for the purposes described herein. Skirt 608 includes a first end 609 connected to tethers 602 and a second end 607 connected to valve component 640. In the embodiment shown, skirt 608 is a cylindrical tube constructed of cloth or fabric material. The fabric may comprise any suitable material including, but not limited to, woven polyester such as polyethylene terepthalate, polytetrafluoroethylene (PTFE), or other biocompatible material. Tethers 602 may be connected to anchor stent 610 by tying, fusion, or other connectors that permit tethers 602 to move as described below. Similarly, skirt 608 may be attached to valve component 640 using sutures or other connectors that permit skirt 608 to move relative to valve component 640, as described below. Tethers 602 may be attached to skirt 608 be tying or suturing tethers 602 to skirt 608, or by other connectors suitable for the purposes described herein. Additionally, the tethers 602 may be tied at a first end 604 coupled to anchor stent 610, tied to a second point on the end 606 of the skirt 608, and tied to a third point 607 on valve component 640.

While the embodiment of FIG. 14 provides a possible configuration for tethers 602 and skirt 608, it is not meant to limit the component to this configuration, and other materials, shapes and combinations of skirts and/or tethers may be utilized depending on the application.

Valve component 640 includes a frame 642 and a prosthetic valve 650. Frame 642 is a generally tubular configuration having a proximal end 646, a distal end 644, and a lumen 643 there between. Frame 642 may be a stent structure as is known in the art. Frame 642 may be self-expanding or may be balloon expandable. Generally, frame 642 includes a first, radially compressed configuration for delivery and a second, radially expanded or deployed configuration when deployed at the desired site. In the radially expanded configuration, frame 642 may have a diameter in the range of 23 to 31 millimeters. In the embodiment shown in FIG. 14, distal end 644 and proximal end 646 of frame 642 have different diameters, similar to valve prosthesis 100 shown in FIG. 1. However, distal end 644 and proximal end 646 may instead have similar expanded diameters. Further, the diameter may be larger or smaller than the range provided above depending on the application. Valve component 640 is configured to be disposed such that prosthetic valve 650 is disposed approximately at the location of the native aortic valve.

As explained briefly above and in more detail below, integrated valve assembly 600 includes anchor stent 610, tethers 602, skirt 608, and valve component 640. Anchor stent 610 is configured to be disposed in the aorta, with proximal arm component 620 extending into the aortic root or aortic sinuses. Valve component 640 is configured to be disposed such that prosthetic valve 650 is disposed approximately at the location of the native aortic valve with proximal end 646 of frame 642 separating the valve leaflets of the native aortic valve. Distal end 644 of frame 642 extends into lumen 613 of frame 612 of anchor stent 610 and is held in place by the outward radial force of frame 642 and frictional forces between frame 642 of valve component and frame 612 of anchor stent 610. Further, an inner surface of frame 612 and/or an outer surface of frame 642 may include locking features such as barbs, anti-migration tabs or other devices known to the art to interconnect with anchor frame 612. For example, and not by way of limitation, barbs 611 shown in FIG. 14A may extend from an inner surface of anchor stent 610. Further, proximal arm component 620 provides support for anchor stent 610 within the aortic sinuses, as described in more detail below.

FIGS. 15-23 schematically represent a method of delivering and deploying integrated valve assembly 600 in accordance with an embodiment hereof. FIGS. 15-23 are not drawn to scale.

Figure 15:
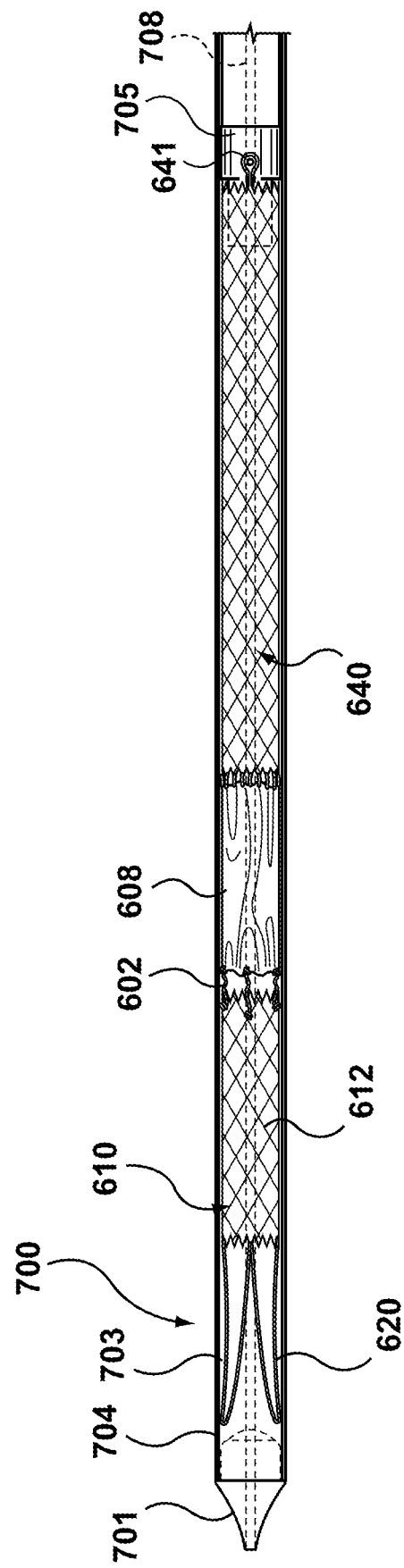
FIG. 15 is a schematic illustration of a distal portion of a delivery device with the integrated valve assembly of FIG. 14 disposed therein.

FIG. 15 shows a distal portion of an exemplary delivery system 700 to deliver and deploy integrated valve prosthesis 600. Delivery system 700 may be similar to other delivery devices for delivery and deployment of valve prostheses. Accordingly, the proximal portion of delivery system 700 is not described herein, but may included features such as handles and knobs to advance delivery system 700, retract sheath 704, and release valve component 640 from hub 705. Delivery system 700 may include, among other features, an inner or guidewire shaft 708 which includes a guidewire lumen for receiving a guidewire 702, a distal tip 701, an outer sheath 704 defining a capsule 703, and a hub 705. A proximal end of guidewire 702 may be backloaded into the guidewire lumen of inner shaft 708 through a distal opening tip 701. Delivery system 700 may be an over-the-wire type catheter, or a rapid exchange catheter, or other known catheter devices. Outer sheath 704 maintains anchor stent 610 and valve component 640 in the radially compressed or delivery configuration during intraluminal delivery through the vasculature, as shown in FIG. 15. Hub 705 may include grooves or other features to mate with tabs 641 disposed at a distal end of valve component 640. Hub 705 and tabs 641 may be features as described, for example and not by way of limitation, in U.S. Patent Application Publication Nos. 2011/0264203; 201/0251675; 2011/0098805; 2010/0049313; and 2009/0287290; and in U.S. Pat. Nos. 8,398,708; 8,052,732; and 6,267,783, each of which is incorporated by reference herein in its entirety. However, delivery system 700 may include different features to retain and subsequently release valve component 640. Further, delivery system 700 may alternatively include a pusher or stopper as described above with respect to delivery system 500. Delivery system 700 may also include other features known to those skilled in the art. Delivery system 700 and/or anchor stent 610 may also include, for example, radiopaque markers such that the clinician may determine when delivery system 700 and/or anchor stent 610 is in the proper location for deployment.

As described previously with respect to FIG. 5, a guidewire 702 is advanced distally, i.e., away from the clinician, through the aorta 400 into the aortic sinuses 412 in the region of the aortic valve 414. Guidewire 702 may be introduced through an opening or arteriotomy through the wall of femoral artery in the groin region of the patient by methods known to those skilled in the art, such as, but not limited to, the Seldinger technique. Guidewire 702 is advanced into the descending (or abdominal) aorta 406, the aortic arch 404, and the ascending aorta 402. Although FIGS. 15-23 show a retrograde percutaneous femoral procedure, it is not meant to limit the method of use and other procedural methods may be used. For example, and not by way of limitation, retrograde percutaneous implantation via subclavian/axillary routes, direct apical puncture, and the use of direct aortic access via either ministernotomy or right anterior thoracotomy may also be used.

Figure 18:
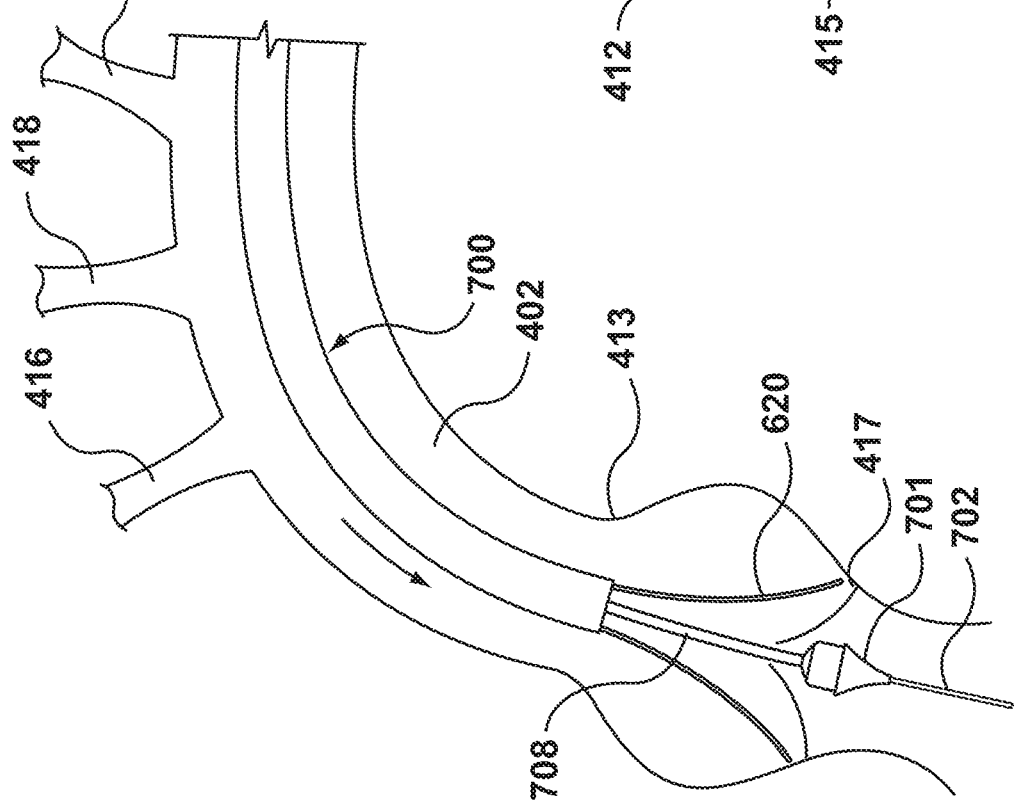

Delivery system 700 is advanced over guidewire 702, as shown in FIG. 16. Once delivery system 700 has been advanced to the desired location, such as when proximal end 616 of anchor stent is generally aligned with the sinotubular junction 413, outer sheath 704 is retracted proximally, i.e., towards the clinician, as shown in FIG. 17. As outer sheath 704 is retracted, proximal arm component 620 expands radially outward, as shown in FIG. 17. Delivery system 700 is then advanced distally, i.e., away from clinician, until proximal arm component 620 bottoms at the nadir of the aortic valve leaflets 117, as shown in FIG. 18.

Figure 19:
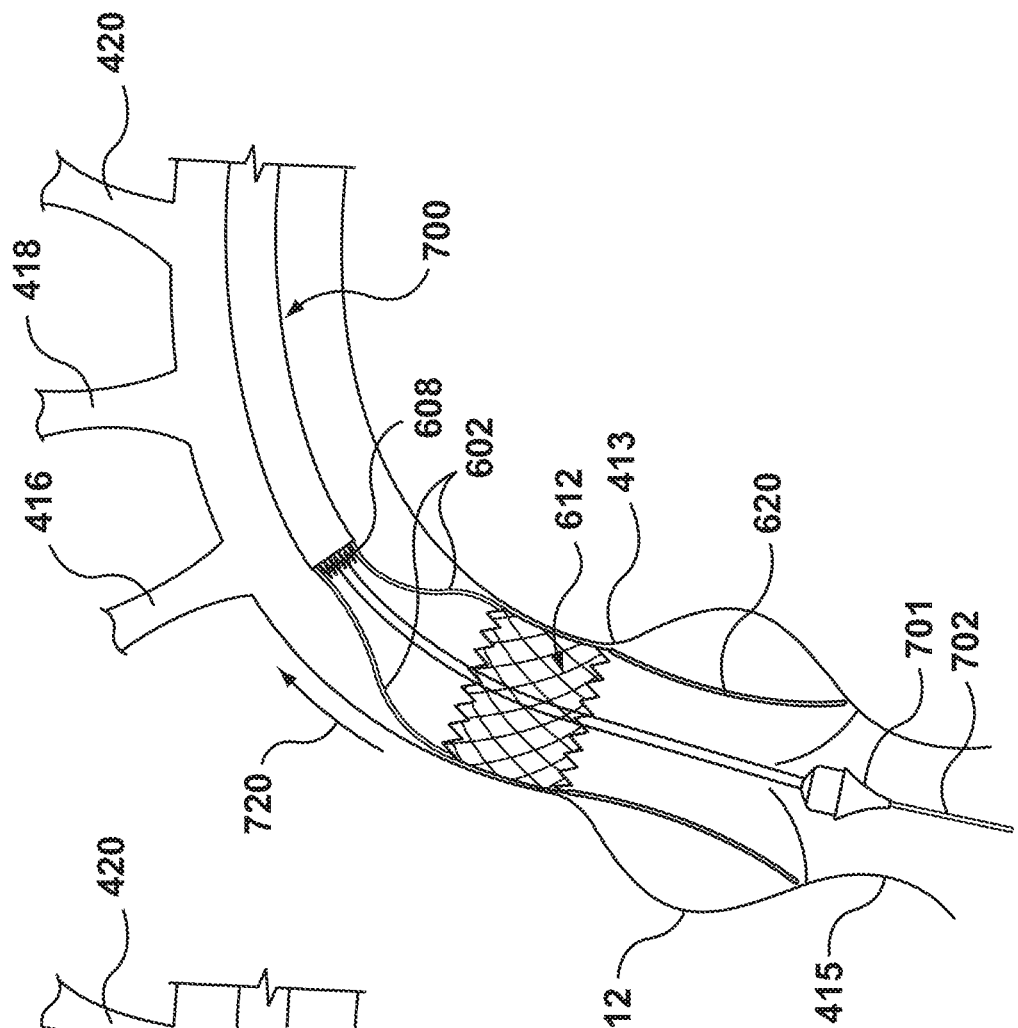

Next, anchor stent 610 is deployed in the aorta near the sinotubular junction 413 by further retracting proximally, i.e., towards the clinician, outer sheath 704 such that tubular frame member 612 expands from the radially compressed configuration to a radially expanded configuration engaging an inner wall surface of the ascending aorta, as shown in FIG. 19.

Although proximal arm component 620 is shown in FIGS. 18-23 as having arms 622, 624, 626 extending to an area near the base of leaflets 414, those skilled in the art would recognize that arms 622, 624, 626 may be shorter such that they engage the sinuses 412 at a location nearer to sinotubular junction 413 than shown in FIGS. 18-23.

As can be seen in FIG. 19, proximal arm component 620 is in the radially expanded configuration such that it flares outwardly from frame 612 and engages the aortic sinuses 412, and frame 612 is in the radially expanded configuration such that it engages the inner wall of the ascending aorta 402.

Figure 20:
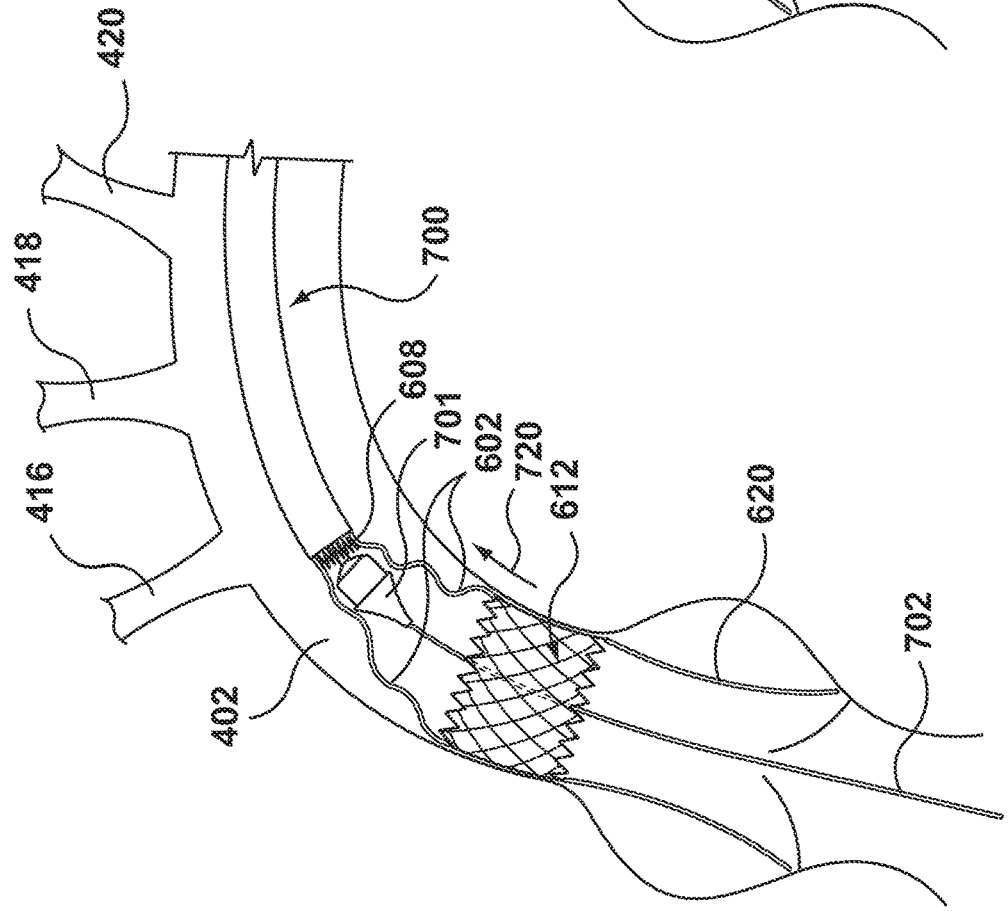

Outer sheath 704 is further retracted proximally, i.e., towards the clinician, to deploy tethers 602 and skirt 608 from outer sheath 704, as shown in FIG. 20. As shown in FIG. 20, tethers 602 and skirt 608 are disposed distal of anchor stent 610 and are not constrained by sheath 704. Tip 701 may then be retracted to near the distal end of sheath 704, as shown in FIG. 20.

Figure 21:
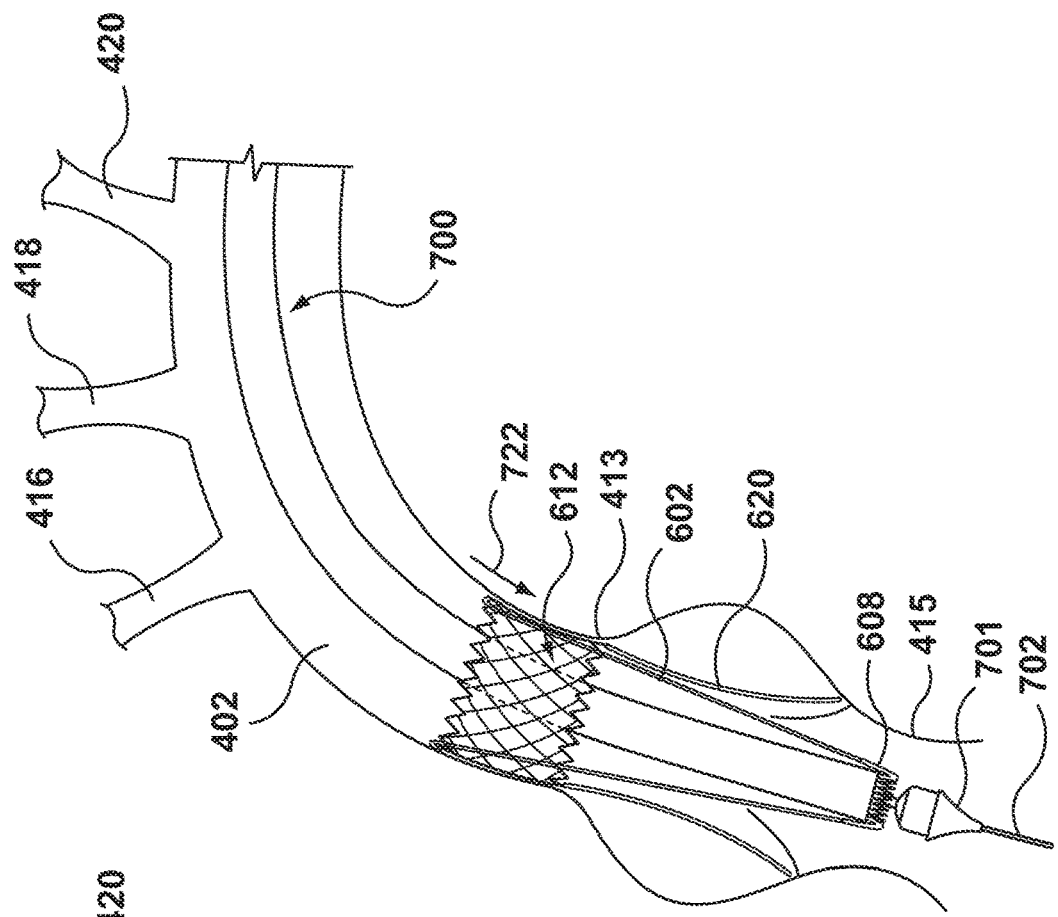

With outer sheath 704 retracted such that anchor stent 610 is deployed in the aorta 400 and tethers 602 and skirt 608 are released from outer sheath 704, delivery system 700 is advanced distally, i.e., away from the clinician, through lumen 613 of anchor frame 612, pulling skirt 608 and tethers 602 through lumen 613, effectively flipping the direction of tethers 602 and skirt 608. Accordingly, whereas tethers 602 and skirt 608 in FIGS. 19-20 extend in a first direction 720 from anchor stent 610 towards valve component 640, tethers 602 and skirt 608 in FIGS. 21-23 extend in a second direction 722 from anchor stent 610 towards valve component 640. Second direction 722 is generally opposite first direction 720. The term "generally opposite" with respect to directions described herein and terms similar thereto, as used herein, is not so narrow as to mean 180 degrees difference in direction. Instead, the term "generally opposite" with respect to direction means that a component includes a vector component in the first direction, the direction which is generally opposite includes a vector component in the opposite direction. Thus, the tethers 602 and skirt 608 in the first direction 720 may be within 45 degrees of the first direction 720 and the second, generally opposite direction 722 may be within 135 degrees to 225 degrees of the first direction 720. Delivery system 700 is advanced distally, i.e., away from the clinician, until tethers 602 and skirt 608 are taut. Tautness of tethers 602 and skirt 608 correctly positions valve component 640 for deployment at desired location, such as near the native aortic valve leaflets 414 and proximal end 646 of frame 642 being generally aligned with the aortic annulus 415, as shown in FIG. 21

Figure 22:
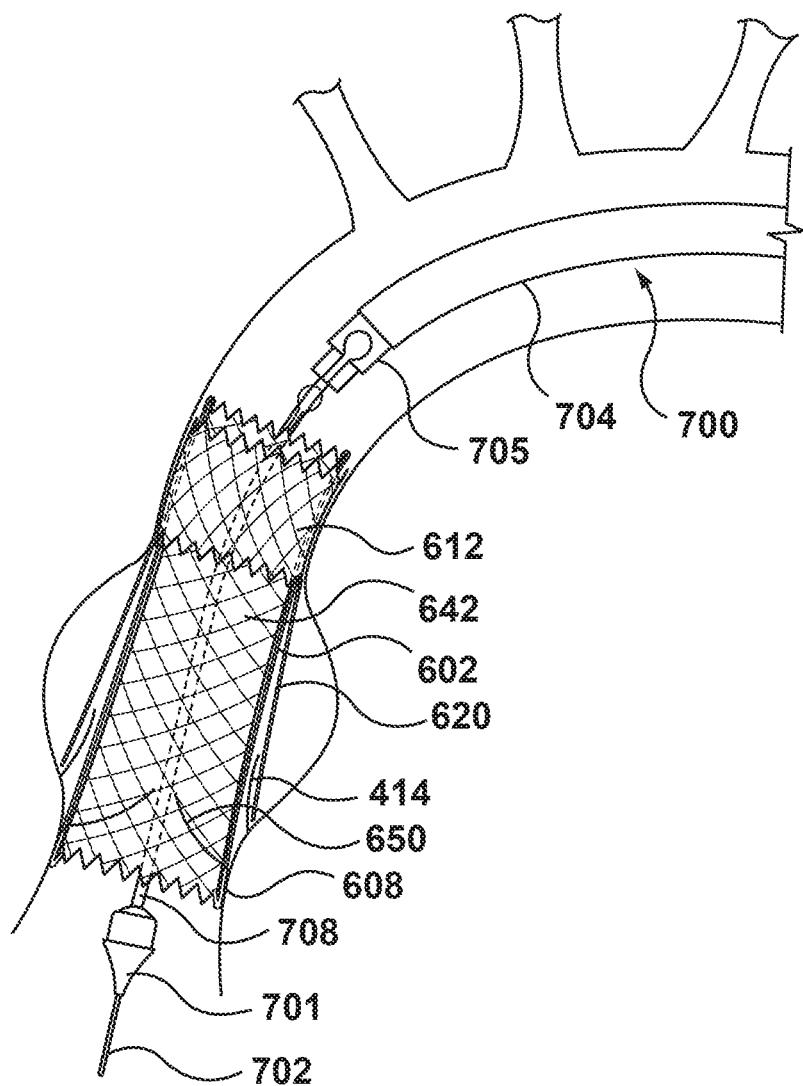
Figure 23:
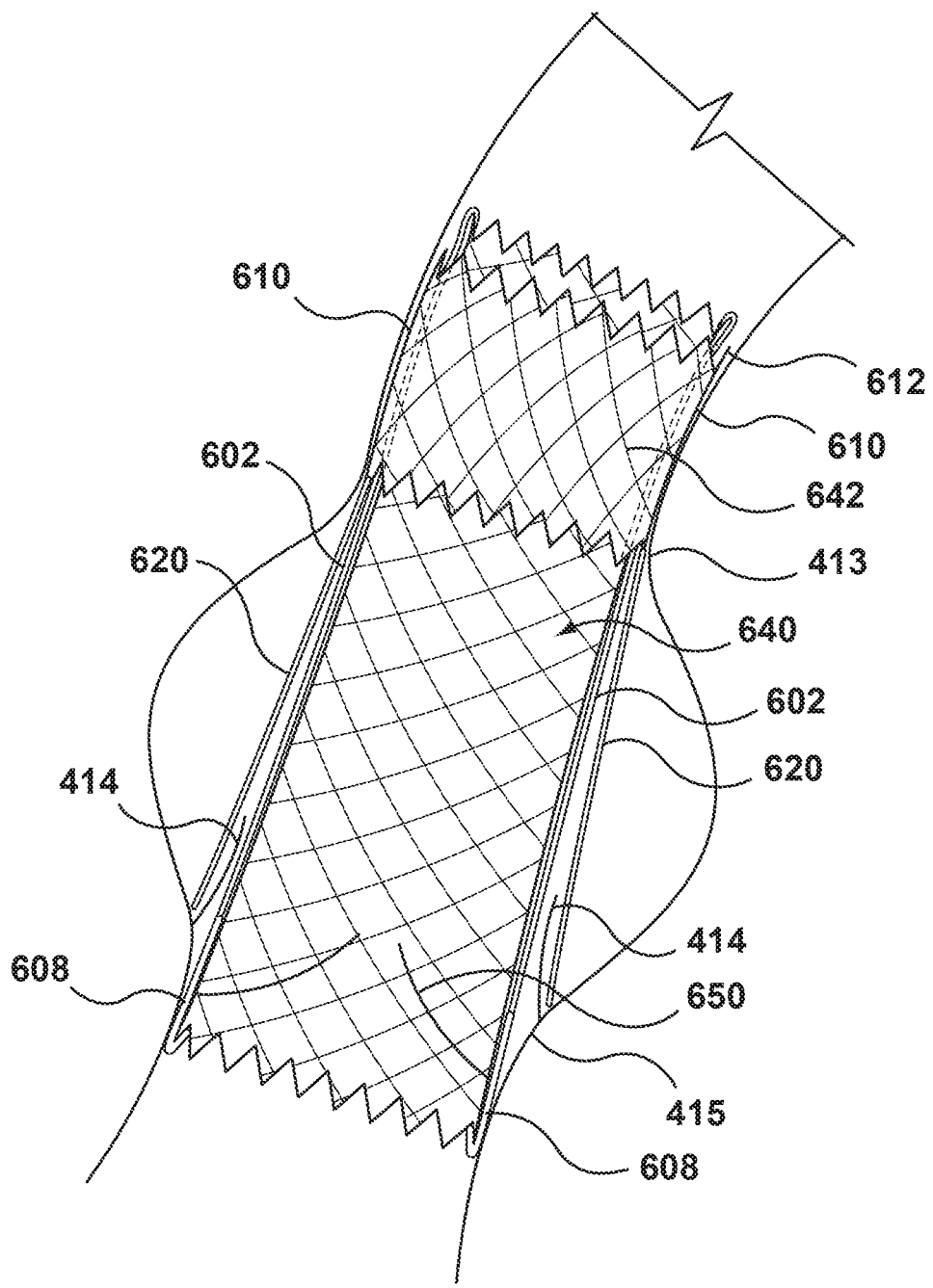

Sheath 704 is then further retracted proximally, i.e., towards the clinician, to deploy frame 642 of valve component 640. Frame 642 expands radially outward to the radially expanded or deployed configuration, as shown in FIGS. 22-23. As frame 642 expands, frame 642 separates the leaflets of native valve 414, as shown in FIGS. 22-23. Proximal end 646 of frame 642 engages the inner wall of the annulus 415, with skirt 608 disposed between frame 642 and the annulus 415. Dist end 644 of frame 642 engages an inner surface of anchor frame 612, as shown in FIGS. 22-23.

With integrated valve prosthesis 600 fully deployed, delivery system 700 and guidewire 702 may be retracted proximally, i.e., towards the clinician, and removed in a manner consistent with current procedures know to those knowledgeable in the art. Integrated valve prosthesis 600 remains in the fully deployed configuration as shown in FIG. 23. FIGS. 16-23 show lateral gaps between the different parts which are disposed adjacent to each other. These gaps are shown for clarity such that the different parts of the integrated valve prosthesis and the heart valve may be seen. It is understood than many of these parts will abut directly against each other due to the radially outward forces of anchor stent 610 and valve frame 642.

Although some examples of advantages have been described above, these are non-limiting in that other advantages of the integrated valve assembly 300/320/600 would be apparent to those skilled in the art.

It will also be understood that each feature of each embodiment discussed herein, and of each reference cited herein, can be used in combination with the features of any other embodiment. All patents and publications discussed herein are incorporated by reference herein in their entirety.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment.

What is claimed is:

1. A method of implanting an integrated valve assembly at a location of a native aortic valve comprising the steps of:
   advancing the integrated valve assembly in a radially compressed configuration into an ascending aorta, wherein the integrated valve assembly comprises an anchor stent, a valve component including a valve frame and a prosthetic valve, and a tether component having a first end coupled to the anchor stent and a second end coupled to the valve component, wherein in the delivery configuration the tether component extends in a first direction from the anchor stent to the valve component;
   deploying the anchor stent from the radially compressed configuration to a radially expanded configuration at a location within the ascending aorta;
   advancing the valve component in the delivery configuration in a second direction opposite the first direction through the anchor stent until the tether component becomes taut; and
   deploying the valve component such that the valve frame expands from the radially compressed configuration to a radially expanded deployed configuration with a first portion of the valve frame engaging the aortic valve.

2. The method of claim 1, wherein the tether component comprises a plurality of tethers.

3. The method of claim 2, wherein the tether component comprises a tubular skirt disposed adjacent the valve component such that the step of advancing the valve component and deploying the anchor component disposes the tubular skirt between the valve component and the annulus of the aortic valve.

4. The method of claim 1, wherein a length of the tether component is configured such that the step advancing the valve component until the tether becomes taut causes at least a portion of the valve component to be disposed within an annulus of the aortic valve.

5. The method of claim 1, wherein the anchor stent further comprises a proximal arm component extending from a proximal end of the anchor stent, wherein the step of deploying the anchor stent comprises deploying the proximal arm component in a sinus of the aortic valve.

6. The method of claim 5, wherein the proximal arm component comprises a plurality of proximal arms and the step of deploying the anchor stent comprises deploying each proximal arm in one of the three aortic sinuses.

7. The method of claim 1, wherein with the anchor stent and the valve component in the deployed configuration, the tether component extends in the second direction from the anchor stent to the valve component.

8. A method of implanting a valve assembly at a location of a native aortic valve comprising the steps of:
   advancing the valve assembly in a radially compressed configuration into an ascending aorta, the valve assembly comprising an anchor stent and a valve component including a valve frame and a prosthetic valve;
   deploying the anchor stent from the radially compressed configuration to a radially expanded configuration at a location within the ascending aorta;
   advancing the valve component in the delivery configuration through the anchor stent; and
   deploying the valve component such that the valve frame expands from the radially compressed configuration to a radially expanded deployed configuration with a first portion of the valve frame engaging an annulus of the aortic valve and a second portion of the valve frame engaging the anchor stent.

9. The method of claim 8, wherein the valve assembly further comprises a tether component, wherein in the delivery configuration the tether component extends in a first direction from the anchor stent to the valve frame, and wherein the step of advancing the valve component through the anchor stent causes the tether component to extend in a second direction opposite the first direction from the anchor stent to the valve frame.

10. The method of claim 9, wherein the valve component is advanced through the anchor stent until the tether component becomes taut.

11. The method of claim 10, wherein a length of the tether component is configured such that the step advancing the valve component until the tether becomes taut causes the first portion of the valve frame to be disposed within the annulus of the aortic valve.

12. The method of claim 9, wherein the tether component comprises a tubular skirt disposed adjacent the valve component such that the step of advancing the valve component and deploying the anchor component disposes the tubular skirt between the valve component and the annulus of the aortic valve.

13. The method of claim 8, wherein the anchor stent further comprises a proximal arm component extending from a proximal end of the anchor stent, wherein the step of deploying the anchor stent comprises deploying the proximal arm component in a sinus of the aortic valve.

14. The method of claim 13, wherein the proximal arm component comprises a plurality of proximal arms and the step of deploying the anchor stent comprises deploying each proximal arm in one of the three aortic sinuses.

* * * * *